US010864222B1

(12) United States Patent
Chen et al.

(10) Patent No.: US 10,864,222 B1
(45) Date of Patent: Dec. 15, 2020

(54) BETA-LACTAMASE INHIBITORS, FORMULATIONS, AND USES THEREOF

(71) Applicants: UNIVERSITY OF SOUTH FLORIDA, Tampa, FL (US); THE REGENTS OF THE UNIVERSITY OF CALIFORNIA, Oakland, CA (US)

(72) Inventors: Yu Chen, Tampa, FL (US); Orville Antonio Pemberton, Tampa, FL (US); Adam Renslo, Oakland, CA (US); Priyadarshini Jaishankar, Newark, CA (US)

(73) Assignees: UNIVERSITY OF SOUTH FLORIDA, Tampa, FL (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/721,090

(22) Filed: Dec. 19, 2019

Related U.S. Application Data

(63) Continuation of application No. 16/050,601, filed on Jul. 31, 2018, now Pat. No. 10,543,221, which is a continuation of application No. PCT/US2017/021905, filed on Mar. 10, 2017.

(60) Provisional application No. 62/307,013, filed on Mar. 11, 2016.

(51) Int. Cl.
| | | |
|---|---|---|
| *A61K 31/675* | (2006.01) | |
| *A61K 31/665* | (2006.01) | |
| *A61P 31/04* | (2006.01) | |
| *C07F 9/655* | (2006.01) | |
| *A61K 31/407* | (2006.01) | |
| *C07F 9/60* | (2006.01) | |
| *C07F 9/6561* | (2006.01) | |
| *A61K 45/06* | (2006.01) | |

(52) U.S. Cl.
CPC .......... *A61K 31/675* (2013.01); *A61K 31/407* (2013.01); *A61K 31/665* (2013.01); *A61K 45/06* (2013.01); *A61P 31/04* (2018.01); *C07F 9/60* (2013.01); *C07F 9/6561* (2013.01); *C07F 9/65522* (2013.01)

(58) Field of Classification Search
CPC ...... A61K 31/675; A61K 31/665; A61P 31/04
USPC .......................................................... 514/82
See application file for complete search history.

(56) References Cited

U.S. PATENT DOCUMENTS

| | | | |
|---|---|---|---|
| 5,342,946 A | 8/1994 | Hamilton | |
| 5,852,195 A | 12/1998 | Romines et al. | |
| 7,183,267 B2 | 2/2007 | Freire et al. | |
| 10,543,221 B2 * | 1/2020 | Chen | A61K 31/407 |
| 2009/0246292 A1 | 10/2009 | Seville et al. | |
| 2011/0245254 A1 | 10/2011 | Aszodi et al. | |
| 2012/0071457 A1 | 3/2012 | Chikauchi et al. | |
| 2013/0079318 A1 | 3/2013 | Buynak et al. | |
| 2014/0256778 A1 | 9/2014 | Freire et al. | |
| 2014/0356375 A1 | 12/2014 | Brown et al. | |

FOREIGN PATENT DOCUMENTS

| | | |
|---|---|---|
| WO | 2009106073 A2 | 9/2009 |
| WO | 2014108832 A1 | 7/2014 |

OTHER PUBLICATIONS

Hamilton; Bioorg. Med. Chem. Lett. 1994, 4, 2035-2040. (Year: 1994).*
Lafitte; Biochemistry 2002, 41, 7217-7223. (Year: 2002).*
Pemberton; J. Med. Chem. 2019, 62, 18, 8480-8496. (Year: 2019).*
Toney, et al. Structure—Activity Relationships of Biphenyl Tetrazoles as Metallo-beta-Lactamase Inhibitors, Bioorganic & Medicinal Chemistry Letters 9 (1999) 2741-2746.
Nichols, et al. Fragment-based inhibitor discovery against beta-lactamase, Future Med Chem 6:4 (Mar. 2014): 413-427.
Chemical Abstracts STN Registry Database, record for RN 1071914-43-6, P-[(5,7-dimethyl-2-oxo-2H-1-benzopyran-4-yl)methyl] Phosphonic acid, entered into database on Nov. 11, 2008. (Year: 2008).
National Center for Biotechnology Information. PubChem Database. ([(5,7-Dimethyl-2-oxo-2H-1-benzopyran-4-yl) methyl] phosphonic acid), MCU LE-7 401451606, Source=Mcule, SID=166221375, https://pubchem.ncbi.nlm.nih.gov/substance/166221375 (accessed on Aug. 15, 2019). Available on Nov. 30, 2013. (Year: 2013).
National Center for Biotechnology Information. PubChem Database. MCU LE-9094429298, SI 0=166219682, Nov. 30, 2013 https://pubchem.ncbi.nlm.nih.gov/substance/166219682 (accessed on Apr. 17, 2019) (Year: 2013).
Safdari; The Journal of Antibiotics (2014) 67, 373-377. (Year: 2014).
Xu; Beilstein J. Org. Chem. 2013, 9, 254-259. (Year: 2013).
Jagodic; Journal of Heterocyclic Chemistry 1980, 17, 685-688. (Year: 1980).
Schwender; Bioorganic & Medicinal Chemistry Letters 1995, 5, 1801-1806. (Year: 1995).
Chemical Abstracts STN Registry Database, record for RN 1071656-52-4, entered into database on Nov. 7, 2008. (Year: 2008).
Chemical Abstracts STN Registry Database, record for RN 1144438-46-9, entered into database on May 8, 2009. (Year: 2009).
Chemical Abstracts STN Registry Database, record for RN 1071915-45-1, entered into database on Nov. 11, 2008. (Year: 2008).
Chemical Abstracts STN Registry Database, record for RN 1071915-10-0, entered into database on Nov. 11, 2008. (Year: 2008).
Chemical Abstracts STN Registry Database, record for RN 1071914-75-4, entered into database on Nov. 11, 2008. (Year: 2008).

(Continued)

*Primary Examiner* — Daniel R Carcanague
(74) *Attorney, Agent, or Firm* — Thomas | Horstemeyer, LLP

(57) ABSTRACT

Provided herein are heterocyclic compounds and pharmaceutical formulations that can be used to treat bacterial infections. Also provided herein are methods of making and using the heterocyclic compounds and pharmaceutical formulations.

18 Claims, 9 Drawing Sheets

(56) References Cited

OTHER PUBLICATIONS

Chemical Abstracts STN Registry Database, record for RN 1071914-04-9, entered into database on Nov. 11, 2008. (Year: 2008).

Chemical Abstracts STN Registry Database, record for RN 501079-97-6, entered into database on Apr. 1, 2003. (Year: 2003).

Chowdhury, et al. Antimicrobial activity of Toona ciiiata and Amoora rohituka. Fitoterapia, vol. 74, 2003, pp. 155-158; p. 156, table 1; p. 157, paragraph 3.

Yam, et aL The effect of a component of tea (Camellia sinensis) on methicillin resistance, PBP2' synthesis, and beta-lactamase production in *Staphylococcus aureus*. Journal of Antimicrobial Therapy, vol. 42, 1998, pp. 211-216; abstract.

Pubchem. Schembl 18279989. Feb. 8, 2007, pp. 1-10 [online], [retrieved on Apr. 25, 2017]. Retrieved from the Internet <URL: https:I/pubchem.ncbi.nim.nih.govtcompound/12629202#section=Top>: pp. 3-5.

Pubchem. Schembl 14007004. Aug. 20, 2012, pp. 1-11 [oniinel, [retrieved on Apr. 25, 2017]. Retrieved from the Internet <URL: ~1ttps://pubchem.ncbi.nlm.ni~1.gov/compound/59841461 #section=Top>; pp. 4, 6.

International Searcll Report for PCT/US2017/021905 dated Mar. 10, 2017.

\* cited by examiner

BETA-LACTAMASE INHIBITORS, FORMULATIONS, AND USES THEREOF

CROSS-REFERENCE TO RELATED APPLICATIONS

This application is a continuation of co-pending U.S. application Ser. No. 16/050,601, filed on Jul. 31, 2018, entitled "BETA-LACTAMASE INHIBITORS, FORMULATIONS, AND USES THEREOF," the contents of which is incorporated by reference herein in its entirety.

U.S. application Ser. No. 16/050,601 is a continuation of PCT Patent Application No.: PCT/US2017/021905, filed on Mar. 10, 2017, entitled "BETA-LACTAMASE INHIBITORS, FORMULATIONS, AND USES THEREOF," the contents of which is incorporated by reference herein in its entirety.

PCT Patent Application No.: PCT/US2017/021905 claims the benefit of and priority to U.S. Provisional Patent Application No. 62/307,013, filed on Mar. 11, 2016, entitled "BETA-LACTAMASE INHIBITORS, FORMULATIONS, AND USES THEREOF," the contents of which is incorporated by reference herein in its entirety.

STATEMENT REGARDING FEDERALLY SPONSORED RESEARCH OR DEVELOPMENT

This invention was made with government support under grant number R0 AI103158 awarded by the National Institutes of Health. The Government has certain rights in the invention.

BACKGROUND

Beta-lactam antibiotics are among the most commonly prescribed antibiotics. Beta-lactam antibiotics target the cross-linking of the bacterial cell wall, which can ultimately result in cell death. Despite the numerous successes of the beta-lactam antibiotics, bacteria have developed resistance to them. As such there exists a need for improved antibacterial treatments to overcome bacterial resistance to beta-lactam antibiotics.

SUMMARY

In some aspects, provided herein are compositions according to Formula 4

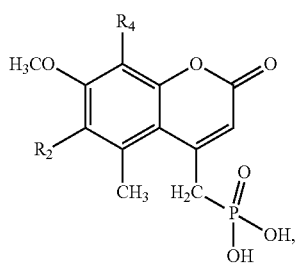

Formula 4 wherein $R_2$ can be selected from the group of H, $CH_3$, Cl, Br, F, $OCH_3$, $CF_3$, an alkyl, a cycloalkyl, and an aryl, and wherein $R_4$ can be selected from the group of H, $CH_3$, Cl, Br, F, $OCH_3$, $CF_3$, an alkyl, a cycloalkyl, and an aryl. In some aspects, $R_2$ can be H and $R_4$ can be H.

Also provide herein are pharmaceutical formulations containing an amount of a composition according to Formula 4, wherein $R_2$ can be selected from the group of H, $CH_3$, Cl, Br, F, $OCH_3$, $CF_3$, an alkyl, a cycloalkyl, and an aryl, and wherein $R_4$ can be selected from the group of H, $CH_3$, Cl, Br, F, $OCH_3$, $CF_3$, an alkyl, a cycloalkyl, and an aryl or wherein $R_2$ can be H and $R_4$ can be H. The pharmaceutical formulations can further include a beta lactam antibiotic. The amount of a composition according to Formula 4 can be an effective amount. The effective amount can increase the efficacy of a beta lactam antibiotic and/or reduce the amount of or the activity of a beta lactamase.

Also provided herein are methods of treating a subject in need thereof, wherein the method can include the step of administering an amount of a composition according to Formula 1

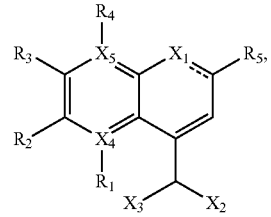

Formula 1 wherein $X_1$ can be O, O⁻, CH, or N—$R_8$, wherein $R_8$ can be H, an alkyl, or a heteroalkyl; wherein $X_2$ can be PO(OH)$_2$, SO(OH)$_2$, CONHOH, COOH, or N(OH)COR$_6$, where $R_6$ can be H or $CH_3$; wherein $X_3$ can be H or SH; wherein $X_4$ can be CH, C, NH, or N⁺; wherein $X_5$ can be CH, or NH; wherein $R_1$ can be H, $CH_3$, Cl, Br, F, $OCH_3$, $CF_3$, an alkyl, a cycloalkyl, or an aryl; wherein $R_2$ can be H, $CH_3$, Cl, Br, F, $OCH_3$, $CF_3$, an alkyl, a cycloalkyl, aryl, or $R_2$ and $R_3$, when taken together with the atoms to which they are attached, can form a cyclic structure having 5 or 6 carbon atoms, one or more of which can be a heteroatom; wherein $R_3$ cam be H, $CH_3$, Cl, Br, F, $OCH_3$, $CF_3$, an alkyl, a cycloalkyl, or an aryl; wherein $R_4$ can be H, $CH_3$, Cl, Br, F, $OCH_3$, $CF_3$, an alkyl, a cycloalkyl, or an aryl; wherein $R_5$ can be H, =O, an alkyl, OR$_7$, NR$_7$, a heteroaryl, or an aryl, where $R_7$ can be H, an alkyl, or a heteroalkyl; and wherein the subject in need thereof can be infected with or suspected of being infected with a pathogenic bacteria. The pathogenic bacteria can express beta lactamase. The pathogenic bacteria can be resistant to at least one beta-lactam antibiotic. The method can further include the step of administering a beta lactam antibiotic to the subject in need thereof. The beta lactam antibiotic can be administered simultaneously or sequentially with the composition according to Formula 1.

In some aspect the composition can have a Formula according to Formula 2

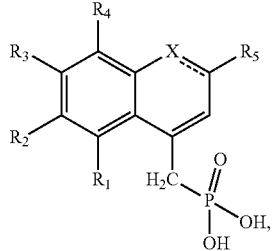

Formula 2 wherein X can be O or N—R_9, wherein R_9 can be H, CH_3, an alkyl, or a heteroalkyl; wherein $R_1$ can be H, CH_3, Cl, Br, F, OCH_3, CF_3, an alkyl, a cycloalkyl, or an aryl; wherein $R_2$ can be H, CH_3, Cl, Br, F, OCH_3, CF_3, alkyl, cycloalkyl, aryl, or $R_2$ and $R_3$, when taken together with the atoms to which they are attached, can form a cyclic structure having 5 or 6 carbon atoms, one or more of which can be a heteroatom; wherein $R_3$ can be H, CH_3, Cl, Br, F, OCH_3, CF_3, an alkyl, a cycloalkyl, or an aryl; wherein $R_4$ can be H, CH_3, Cl, Br, F, OCH_3, CF_3, an alkyl, a cycloalkyl, or an aryl; and wherein $R_5$ can be =O, an alkyl, OR_7, NR_7, a heteroaryl, or an aryl, where $R_7$ can be H, an alkyl or a heteroalkyl.

In some aspects, the composition can have a Formula according to Formula 3

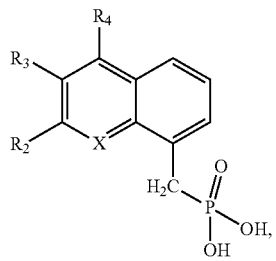

Formula 3 wherein X can be CH, C, NH, N, N^+, N^+—O^-, or NMe; wherein $R_2$ can be H, CH_3, Cl, Br, F, OCH_3, CF_3, an alkyl, a cycloalkyl, or an aryl; wherein $R_3$ can be H, CH_3, Cl, Br, F, OCH_3, CF_3, an alkyl, a cycloalkyl, or an aryl; and wherein $R_4$ can be H, CH_3, Cl, Br, F, OCH_3, CF_3, an alkyl, a cycloalkyl, or an aryl.

In some aspects, the composition can have a Formula according to Formula 4

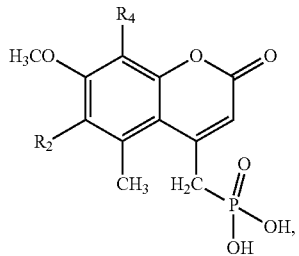

Formula 4 wherein $R_2$ can be H, CH_3, Cl, Br, F, OCH_3, CF_3, an alkyl, a cycloalkyl, or an aryl; and wherein $R_4$ can be H, CH_3, Cl, Br, F, OCH_3, CF_3, an alkyl, a cycloalkyl, or an aryl.

In some aspects, the composition can have a formula according to any one of Formulas 5-19:

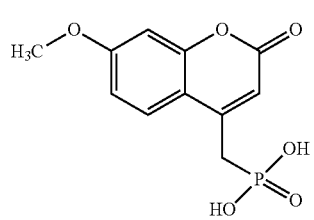

Formula 5

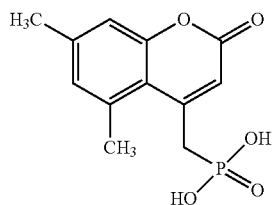

Formula 6

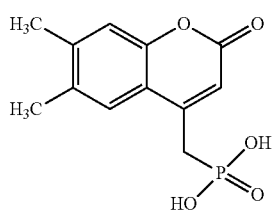

Formula 7

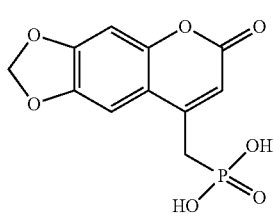

Formula 8

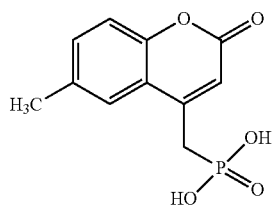

Formula 9

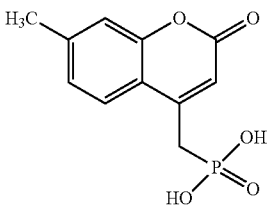

Formula 10

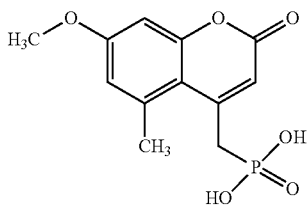

Formula 11

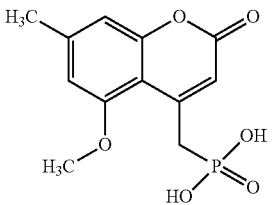

Formula 12

-continued

Formula 13
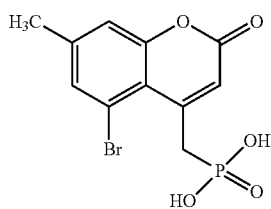

Formula 14
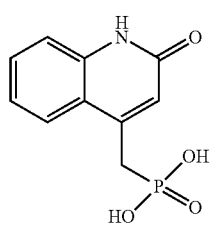

Formula 15
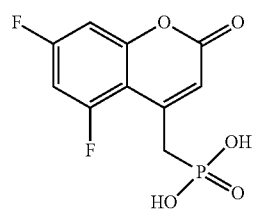

Formula 16
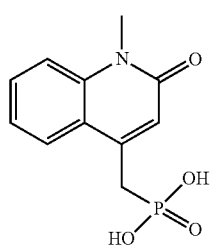

Formula 17
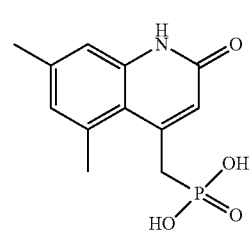

Formula 18
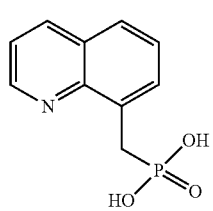

Formula 19
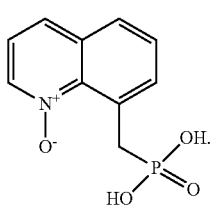

In some aspects, the composition can be included in a pharmaceutical formulation.

In some aspects the composition can be administered orally intravenously, intramuscularly, intravaginally, intraperitoneally, rectally, perenterally, topically, intranasally, or subcutaneously.

Also provided herein are compositions having a structure according to Formula 1, wherein $X_1$ can be O, O$^-$, CH, or N—$R_8$, wherein $R_8$ can be H, an alkyl, or a heteroalkyl; wherein $X_2$ can be PO(OH)$_2$, SO(OH)$_2$, CONHOH, COOH, or N(OH)COR$_6$, where $R_6$ can be H or CH$_3$; wherein $X_3$ can be H or SH; wherein $X_4$ can be CH, C, NH, or N$^+$; wherein $X_5$ can be CH, or NH; wherein $R_1$ can be H, CH$_3$, Cl, Br, F, OCH$_3$, CF$_3$, an alkyl, a cycloalkyl, or an aryl; wherein $R_2$ can be H, CH$_3$, Cl, Br, F, OCH$_3$, CF$_3$, an alkyl, a cycloalkyl, aryl, or $R_2$ and $R_3$, when taken together with the atoms to which they are attached, can form a cyclic structure having 5 or 6 carbon atoms, one or more of which can be a heteroatom; wherein $R_3$ can be H, CH$_3$, Cl, Br, F, OCH$_3$, CF$_3$, an alkyl, a cycloalkyl, or an aryl; wherein $R_4$ can be H, CH$_3$, Cl, Br, F, OCH$_3$, CF$_3$, an alkyl, a cycloalkyl, or an aryl; and wherein $R_5$ is H, =O, an alkyl, OR$_7$, NR$_7$, a heteroaryl, or an aryl, where $R_7$ can be H, an alkyl, or a heteroalkyl. In some aspects, the composition can have a structure according to any one of Formulas 5-19. In some aspects, the composition can have a structure according to Formula 2, wherein X can be O or N—$R_9$, wherein $R_9$ can be H, CH$_3$, an alkyl, or a heteroalkyl; wherein $R_1$ can be H, CH$_3$, Cl, Br, F, OCH$_3$, CF$_3$, an alkyl, a cycloalkyl, or an aryl; wherein $R_2$ can be H, CH$_3$, Cl, Br, F, OCH$_3$, CF$_3$, alkyl, cycloalkyl, aryl, or $R_2$ and $R_3$, when taken together with the atoms to which they are attached, can form a cyclic structure having 5 or 6 carbon atoms, one or more of which can be a heteroatom; wherein $R_3$ can be H, CH$_3$, Cl, Br, F, OCH$_3$, CF$_3$, an alkyl, a cycloalkyl, or an aryl; wherein $R_4$ can be H, CH$_3$, Cl, Br, F, OCH$_3$, CF$_3$, an alkyl, a cycloalkyl, or an aryl; and wherein $R_5$ can be =O, an alkyl, OR$_7$, NR$_7$, a heteroaryl, or an aryl, where $R_7$ can be H, an alkyl, or a heteroalkyl. In some aspects, the composition can have a structure according to Formula 3, wherein X can be CH, C, NH, N, N$^+$, N$^+$—O$^-$, or NMe; wherein $R_2$ can be H, CH$_3$, Cl, Br, F, OCH$_3$, CF$_3$, an alkyl, a cycloalkyl, or an aryl; wherein $R_3$ can be H, CH$_3$, Cl, Br, F, OCH$_3$, CF$_3$, an alkyl, a cycloalkyl, or an aryl; and wherein $R_4$ can be H, CH$_3$, Cl, Br, F, OCH$_3$, CF$_3$, an alkyl, a cycloalkyl, or an aryl.

Also provided herein are compositions that can have a structure according to Formula 20

Formula 20
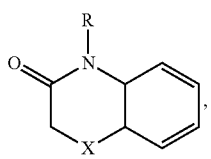

wherein X can be O or N; and R can be H, NH, NMe, or CH$_3$.

Also provided herein are pharmaceutical formulations that can include an amount of a composition according to any one of Formulas 1-20 as provided herein and a pharmaceutically acceptable carrier. The pharmaceutical formulations can further include a beta lactam antibiotic.

The amount of a composition to any one of Formulas 1-20 as provided herein can be an effective amount. The effective amount can increase the efficacy of a beta lactam antibiotic and/or reduce the amount of or the activity of a beta lactamase.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1A:
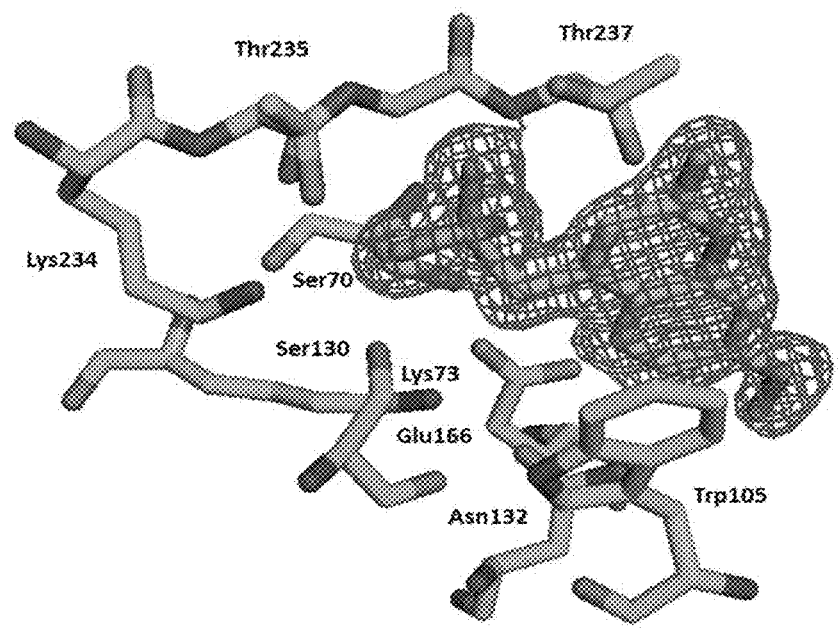
FIGS. 1A-1F show KPC-2 crystal structures of (FIG. 1A) 72875 (Formula 5), (FIG. 1B) 73475 (Formula 8), (FIG. 1C) 72588 (Formula 6), (FIG. 1D) 73043 (Formula 7), (FIG. 1E) 72674 (Formula 9), (FIG. 1F) 994284 (Formula 11), and (FIG. 1G) 994942 (Formula 13).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of organic chemistry, biochemistry, pharmacology, botany, molecular biology, microbiology, medicinal chemistry and the like, which are within the skill of the art. Such techniques are explained fully in the literature.

DEFINITIONS

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used herein, "control" is an alternative subject or sample used in an experiment for comparison purposes and included to minimize or distinguish the effect of variables other than an independent variable. A "control" can be positive or negative.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "active agent" or "active ingredient" refers to a component or components of a composition to which the whole or part of the effect of the composition is attributed.

As used herein, "dose," "unit dose," or "dosage" refers to physically discrete units suitable for use in a subject, each unit containing a predetermined quantity of the nanoparticle composition or formulation calculated to produce the desired response or responses in association with its administration.

As used herein "immunomodulator," refers to an agent, such as a therapeutic agent, which is capable of modulating or regulating one or more immune function or response.

As used herein "anti-infectives" can include, but are not limited to, antibiotics, antibacterials, antifungals, antivirals, and antiproatozoals.

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters, amides, hydroxamic acids, or hydrazides. Derivatives include compounds in which hydroxyl groups in the parent compound have been derivatized to form O-acyl, O-carbamoyl, or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring, as an example, with saturated or unsaturated cyclohexane or other more complex, e.g., nitrogen-containing rings, and extensions of these rings with various groups.

As used herein, "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

As used herein, "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl)$C_1$-$C_6$ alkoxy, $C_3$-$C_7$ heterocycloalkyl, ($C_3$-$C_7$ heterocycloalkyl)$C_1$-$C_6$ alkyl, ($C_3$-$C_7$ heterocycloalkyl) $C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, aralkyl, heteroaralkyl, aralkoxy, heteroaralkoxy, nitro, cyano, amino, $C_1$-$C_6$ alkylamino, di-($C_1$-$C_6$ alkyl) amino, carbamoyl, ($C_1$-$C_6$ alkyl)carbonyl, ($C_1$-$C_6$ alkoxy) carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl) sulfonyl, and arylsulfonyl. The groups listed above as suitable substituents are as defined hereinafter except that a suitable substituent may not be further optionally substituted.

As used herein, "optionally substituted" indicates that a group may be unsubstituted or substituted with one or more substituents as defined herein.

The term "alkyl" refers to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl can have 30 or fewer carbon atoms in its backbone (e.g., $C_1$-$C_{30}$ for straight chains, and $C_3$-$C_{30}$ for branched chains). In other embodiments, a straight chain or branched chain alkyl can contain 20 or fewer, 15 or fewer, or 10 or fewer carbon atoms in its backbone. Likewise, in some embodiments cycloalkyls can have 3-10 carbon atoms in their ring structure. In some of these embodiments, the cycloalkyl can have 5, 6, or 7 carbons in the ring structure.

The term "alkyl" (or "lower alkyl") as used herein is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls can be substituted in the same manner.

The term "heteroalkyl," as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy," as used herein, refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

The terms "amine" and "amino" (and its protonated form) are art-recognized and refer to both unsubstituted and substituted amines, e.g., a moiety that can be represented by the general formula:

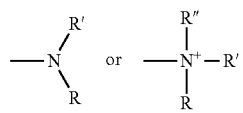

wherein R, R', and R" each independently represent a hydrogen, an alkyl, an alkenyl, —(CH$_2$)$_m$—R$_C$ or R and R' taken together with the N atom to which they are attached complete a heterocycle having from 4 to 8 atoms in the ring structure; R$_C$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloalky, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

The term "amido" is art-recognized as an amino-substituted carbonyl and includes a moiety that can be represented by the general formula:

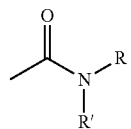

wherein R and R' are as defined above.

As used herein, "Aryl" refers to C$_5$-C$_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

The term "aralkyl," as used herein, refers to an alkyl group substituted with an aryl group (e.g., an aromatic or heteroaromatic group).

The term "aralkyloxy" can be represented by —O-aralkyl, wherein aralkyl is as defined above.

The term "carbocycle," as used herein, refers to an aromatic or non-aromatic ring(s) in which each atom of the ring(s) is carbon.

"Heterocycle" or "heterocyclic," as used herein, refers to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbonyl" is art-recognized and includes such moieties as can be represented by the general formula:

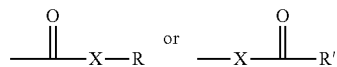

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

The term "heteroatom" as used herein means an atom of any element other than carbon or hydrogen. Exemplary heteroatoms include, but are not limited to, boron, nitrogen, oxygen, phosphorus, sulfur, silicon, arsenic, and selenium. Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, the term "nitro" refers to —$NO_2$; the term "halogen" designates —F, —Cl, —Br, or —I; the term "sulfhydryl" refers to —SH; the term "hydroxyl" refers to —OH; and the term "sulfonyl" refers to —$SO_2$—.

As used herein, "effective amount" refers to the amount of a composition described herein or pharmaceutical formulation described herein that will elicit a desired biological or medical response of a tissue, system, animal, plant, protozoan, bacteria, yeast or human that is being sought by the researcher, veterinarian, medical doctor or other clinician. The desired biological response can be death, growth inhibition, reproductive inhibition, and/or development inhibition. The effective amount will vary depending on the exact chemical structure of the composition or pharmaceutical formulation, the causative agent and/or severity of the infection, disease, disorder, syndrome, or symptom thereof being treated or prevented, the route of administration, the time of administration, the rate of excretion, the drug combination, the judgment of the treating physician, the dosage form, and the age, weight, general health, sex and/or diet of the subject to be treated. "Effective amount" can refer to an amount of a composition or pharmaceutical formulation described herein that can increase the efficacy of a beta lactam antibiotic and/or reduce amount or activity of a beta lactamase Discussion One of the most extensively studied bacterial resistance mechanisms is resistance to beta-lactam antibiotics such as pencillins, cephalosporins, and carbapenems. Beta-lactam antibiotics are among the most commonly prescribed antibiotics in the clinical setting. Beta-lactam antibiotics target the cross-linking of the bacterial cell wall, which ultimately results in cell death. Despite the numerous successes of the beta-lactam antibiotics, bacteria have developed resistance to them, most often through the production of enzymes known as beta-lactamases. Beta-lactamases are divided into four groups (class A, B, C, and D) based on their mechanism of action and amino acid similarity. Class A, C, and D beta-lactamases are serine enzymes that use an active site serine residue to hydrolyze the beta-lactam ring, whereas class B beta-lactamases are metallo-enzymes that use one or two zinc ions to carry out the hydrolysis reaction.

Since the introduction of benzylpenicillin in the early 1940s and the emergence of resistance a few years later, numerous semisynthetic beta-lactam antibiotics such as cephalosporins and carbapenems were developed that were more stable to beta-lactamase hydrolysis; however, as previously observed, resistance to these beta-lactam antibiotics is now extensive.

Combining a beta-lactamase inhibitor with a beta-lactam antibiotic has been the most successful approach in extending the efficacy of beta-lactam antibiotics; however, the clinically relevant beta-lactamase inhibitors, clavulanic acid, sulbactam, and tazobactam are most effective only against class A beta-lactamases. In addition, these inhibitors possess a beta-lactam ring, which can induce beta-lactamase expression and increase their susceptibility to hydrolysis. To address the prevalence of ESBLs and carbapenemases, as well as inhibitor resistant beta-lactamases, improved broad-spectrum beta-lactamase inhibitors are urgently needed.

With that said, described herein are heterocyclic compounds, formulations, and that can inhibit beta-lactamase, such as KPC-2 and NDM-1. Use of a heterocyclic compound that can function as a broad-spectrum beta-lactamase inhibitor has had limited investigation. Because KPC-2 and NDM-1 beta-lactamases are implicated in multi-drug resistant infections, an inhibitor targeting these enzymes would be of therapeutic interest. Also described herein are methods of making and using the heterocyclic compounds and formulations described herein. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Heterocyclic Compounds and Formulations Thereof
Heterocyclic Compounds

Provided herein are compounds according to Formula 1, where $X_1$ can be O, O⁻, CH, or N—$R_8$, wherein $R_8$ can be H, an alkyl, or a heteroalkyl; $X_2$ can be $PO(OH)_2$, $SO(OH)_2$, $CONHOH$, $COOH$, or $N(OH)COR_6$, where $R_6$ can be H or $CH_3$; $X_3$ can be H or SH; $X_4$ can be CH, C, NH, or N⁺; $X_5$ can be CH, or NH; $R_1$ can be H, $CH_3$, Cl, Br, F, $OCH_3$, $CF_3$, an alkyl, a cycloalkyl, or an aryl; $R_2$ can be H, $CH_3$, Cl, Br, F, $OCH_3$, $CF_3$, an alkyl, a cycloalkyl, aryl, or $R_2$ and $R_3$, when taken together with the atoms to which they are attached, can form a cyclic structure having 5 or 6 carbon atoms, one or more of which can be a heteroatom; $R_3$ can be H, $CH_3$, Cl, Br, F, $OCH_3$, $CF_3$, an alkyl, a cycloalkyl, or an aryl; $R_4$ can be H, $CH_3$, Cl, Br, F, $OCH_3$, $CF_3$, an alkyl, a cycloalkyl, or an aryl; $R_5$ can be H, =O, an alkyl, $OR_7$, $NR_7$, a heteroaryl, or an aryl, where $R_7$ can be H, an alkyl (such as a $C_1$-$C_{12}$ alkyl), or a heteroalkyl.

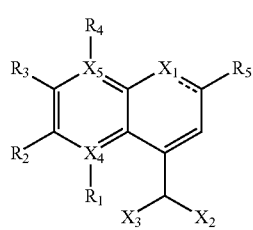

Formula 1

In some embodiments, the composition can have a formula according to any one of Formulas 5-19. In embodiments, Formula 1, its derivatives, or any of its substituents can be further substituted with a suitable substituent.

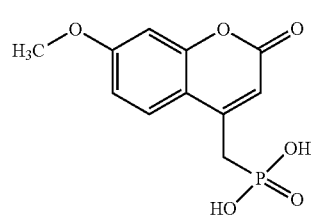

Formula 5

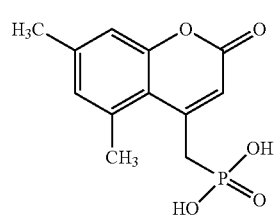

Formula 6

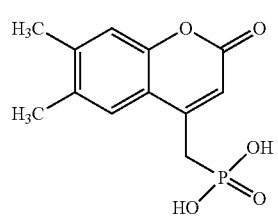

Formula 7

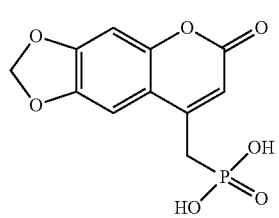

Formula 8

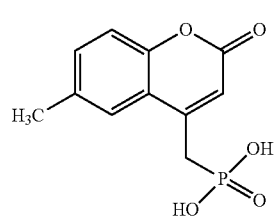

Formula 9

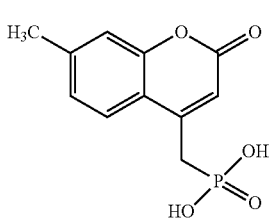

Formula 10

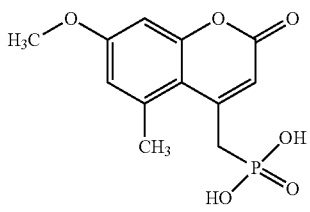

Formula 11

-continued

Formula 12
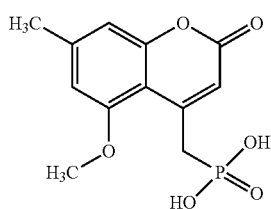

Formula 13
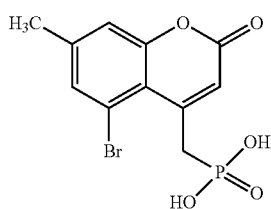

Formula 14
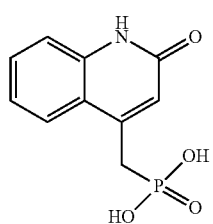

Formula 15
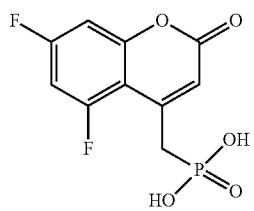

Formula 16
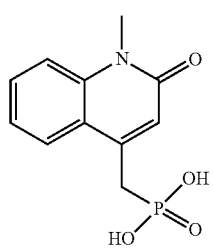

Formula 17
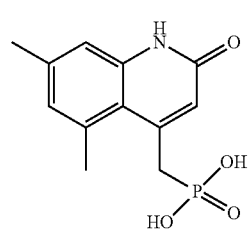

Formula 18
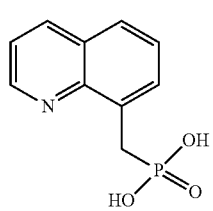

-continued

Formula 19
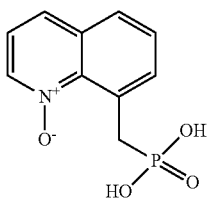

Also provided herein are compounds according to Formula 2, where X can be O or N—$R_9$, wherein $R_9$ can be H, $CH_3$, an alkyl, or a heteroalkyl; $R_1$ can be H, $CH_3$, Cl, Br, F, $OCH_3$, $CF_3$, an alkyl, a cycloalkyl, or an aryl; $R_2$ can be H, $CH_3$, Cl, Br, F, $OCH_3$, $CF_3$, alkyl, cycloalkyl, aryl, or $R_2$ and $R_3$, when taken together with the atoms to which they are attached, can form a cyclic structure having 5 or 6 carbon atoms, one or more of which can be a heteroatom; $R_3$ can be H, $CH_3$, Cl, Br, F, $OCH_3$, $CF_3$, an alkyl, a cycloalkyl, or an aryl; $R_4$ can be H, $CH_3$, Cl, Br, F, $OCH_3$, $CF_3$, an alkyl, a cycloalkyl, or an aryl; and $R_5$ can be =O, an alkyl, $OR_7$, $NR_7$, a heteroaryl, or an aryl, where $R_7$ can be H, an alkyl (such as a $C_1$-$C_{12}$ alkyl), or a heteroalkyl.

Formula 2
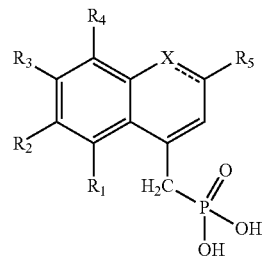

In embodiments, Formula 2, its derivatives, or any of its substituents can be further substituted with a suitable substituent. In some embodiments, the compounds that can have a structure according to Formula 2 can be any one of compounds according to any one of Formulas 5, 6, 7, 8, 9, 10, 11, 12, 13, 14, 15, 16, and 17.

Also provided herein are compounds according to Formula 3, where X can be CH, C, NH, N, $N^+$, $N^+$—$O^-$, or NMe, $R_2$ can be H, $CH_3$, Cl, Br, F, $OCH_3$, $CF_3$, an alkyl, a cycloalkyl, or an aryl; $R_3$ can be H, $CH_3$, Cl, Br, F, $OCH_3$, $CF_3$, an alkyl, a cycloalkyl, or an aryl; and $R_4$ can be H, $CH_3$, Cl, Br, F, $OCH_3$, $CF_3$, an alkyl, a cycloalkyl, or an aryl.

Formula 3
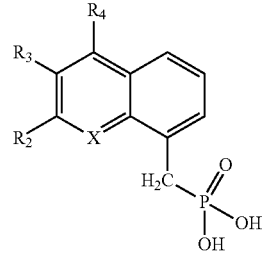

In embodiments, Formula 3, its derivatives, or any of its substituents can be further substituted with a suitable substituent. In some embodiments, the compounds that can have a structure according to Formula 3 can be any one of compounds according to any one of Formulas 18 or 19.

Also provided herein are compounds according to Formula 4, where $R_2$ can be H, $CH_3$, Cl, Br, F, $OCH_3$, $CF_3$, an alkyl, a cycloalkyl, or an aryl and $R_4$ can be H, $CH_3$, Cl, Br, F, $OCH_3$, $CF_3$, an alkyl, a cycloalkyl, or an aryl.

Methods of Making the Heterocyclic Compounds

The compounds described herein are commercially available or can be synthesized using techniques known to those skilled in the art.

Preparation of [(7-methoxy-5-methyl-2-oxo-2H-chromen-4-yl)methyl]phosphonic acid (Formula 11)

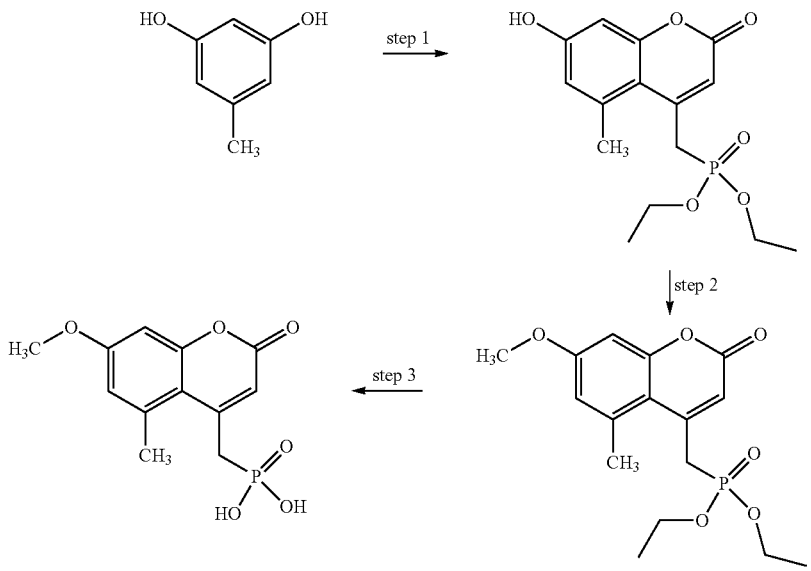

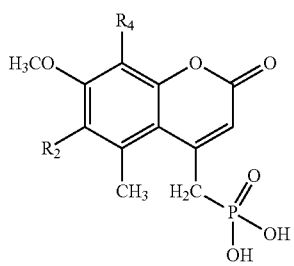

Formula 4

In some embodiments, $R_2$ and $R_4$ can both be H. In embodiments, Formula 4, its derivatives, or any of its substituents can be further substituted with a suitable substituent. In some embodiments, the compounds that can have a structure according to Formula 3 can be a compound according to Formulas 5.

Also provided herein are compounds that can have a structure according to Formula 20, where X can be O or N and R can be H, NH, NMe, or $CH_3$.

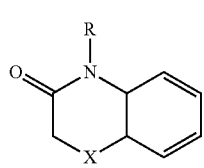

Formula 20

Step 1: Diethyl [(7-hydroxy-5-methyl-2-oxo-2H-chromen-4-yl)methyl]phosphonate

Ethyl 4-(diethoxyphosphoryl)-3-oxobutanoate (0.250 g, 0.9 mmol) was added to concentrated sulfuric acid (0.250 ml) with stirring at 0° C. To the mixture was added 5-methylresorcinol (0.118 g, 0.9 mmol) and the mixture was stirred at room temperature for 18 h. Cold water was then added to the reaction mixture and the precipitate was collected by filtration, and dried to afford 230 mg of the product as a pale pink solid.

1H NMR: (400 MHz, $CDCl_3$) 6.56 (s, 1H), 6.32 (s, 1H), 6.05 (s, 1H), 4.15 (q, J=7.3 Hz, 4H), 3.79 (s, 1H), 3.73 (s, 1H), 2.12 (s, 3H), 1.33 (t, J=6.8 Hz, 6H).

Step 2. Diethyl [(7-methoxy-5-methyl-2-oxo-2H-chromen-4-yl)methyl]phosphonate

The product of step 1, diethyl [(7-hydroxy-5-methyl-2-oxo-2H-chromen-4-yl)methyl]phosphonate (0.020 g, 0.1 mmol, 1.0 equiv.) was taken into methanol (0.3 mL) and treated with 2M solution of (trimethylsilyl)diazomethane in hexanes (0.306 ml, 0.6 mmol, 10.0 equiv.) and stirred at room temperature for 18 h. After this time the reaction was 30% complete as judged by LC/MS. An additional portion (20 eq) of (trimethylsilyl)diazomethane solution was added and the reaction mixture stirred at room temperature for another 72 h. The reaction mixture was then diluted with ethyl acetate and washed with sat.$NaHCO_3$, water & brine. The organic phase was dried over magnesium sulfate, filtered, and concentrated to afford the crude product, which was purified by flash column chromatography (100% ethyl acetate/hexanes followed by 0-5% methanol/dichloromethane followed by 5% methanol/dichloromethane) to obtain 16 mg of the product as pale yellow solid.

1H NMR: (400 MHz, CDCl$_3$) 6.8 (s, 1H), 6.59 (s, 1H), 6.18 (d, J=4.6 Hz, 1H), 4.07-4.10 (m, 4H), 3.95 (s, 3H), 3.70-3.73 (m, 2H), 2.38 (s, 3H), 1.26 (t, J=7.1 Hz, 6H).

Step 3. [(7-methoxy-5-methyl-2-oxo-2H-chromen-4-yl)methyl]phosphonic acid

To the product of Step 2, diethyl [(7-methoxy-5-methyl-2-oxo-2H-chromen-4-yl)methyl]phosphonate (0.013 g, 0.0 mmol) was added a solution of 4M HCl in dioxane (0.4 mL) and the reaction mixture heated at 100° C. for 2 h. Another portion (0.2 mL) of 4M HCl in dioxane was added and the mixture stirred at 100° C. for another hour. The solution was then cooled to room temperature, concentrated, and triturated with ethyl acetate. The mixture was vortexed & the ethyl acetate layer decanted. This procedure was repeated three times and the remaining solid was dried to obtain 6.2 mg of the product as a beige powder.

1H NMR: (400 MHz, d$_6$-DMSO) 6.8 (d, J=1.5 Hz, 2H), 6.12 (d, J=4.6 Hz, 1H), 3.87 (s, 3H), 3.55-3.61 (m, 2H), 2.38 (s, 3H).

Pharmaceutical Formulations

Also provided herein are pharmaceutical formulations that can an amount of a heterocyclic compound or derivative thereof described herein in a pharmaceutically acceptable carrier appropriate for administration to an individual in need thereof. The individual in need thereof can have or can be suspected of having a bacterial infection. The individual in need thereof can be or suspected of being infected with a bacteria that is resistant to one or more beta lactam antibiotics. Formulations can be administered via any suitable administration route. For example, the formulations (and/or compositions) can be administered to the subject in need thereof orally, intravenously, intramuscularly, intravaginally, intraperitoneally, rectally, parenterally, topically, intranasally, or subcutaneously. Other suitable routes are described herein. The heterocyclic compound(s) contained in the pharmaceutical formulation can have a formula according to any one of Formulas 1-20 or a derivative thereof as set forth in the description and Examples provided herein.

Parenteral Formulations

The heterocyclic compounds and derivatives thereof can be formulated for parenteral delivery, such as injection or infusion, in the form of a solution or suspension. The heterocyclic compound(s) and/or derivative(s) thereof contained in the pharmaceutical formulation can have a formula according to any one of Formulas 1-20, a derivative thereof encompassed by the description and Examples provided herein, or a pharmaceutical salt thereof. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the heterocyclic compound(s) or derivative(s) thereof as described herein can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of the heterocyclic compound or derivate thereof.

The formulation can be buffered to a pH of 3-8 for parenteral administration upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating the autophagic inhibitor or active derivative thereof in the required amount in the appropriate solvent or dispersion medium with one or more of the excipients listed above, as required, followed by filtered sterilization. Dispersions can be prepared by incorporating the various sterilized autophagic inhibitor or derivative thereof into a sterile vehicle which contains the basic dispersion medium and the required other ingredients from those listed above. Sterile powders for the preparation of sterile injectable solutions can be prepared by vacuum-drying and freeze-drying techniques, which yields a powder of the autophagic inhibitor or active derivative thereof plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of particles formed from one or more heterocyclic compounds and/or derivatives thereof. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other embodiments, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for parenteral administration can also contain one or more excipients, such as dispersing agents, wetting agents, and suspending agents.

Topical Formulations

The heterocyclic compounds and/or derivative(s) thereof as described herein can be formulated for topical administration. The heterocyclic compound can have a formula according to any of Formulas 1-20. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some embodiments, the heterocyclic compounds and/or derivatives thereof can be administered as a liquid formulation, such as a solution or suspension, a semi-solid formulation, such as a lotion or ointment, or a solid formulation. In some embodiments, the heterocyclic compounds and/or derivatives thereof can be formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like.

Suitable emollients include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some embodiments, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some embodiments, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some embodiments, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. In some embodiments, the surfactant can be a non-ionic surfactant. In other embodiments, the emulsifying agent is an emulsifying wax. In further embodiments, the liquid non-volatile non-aqueous material is a glycol. In some embodiments, the glycol is propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing a heterocyclic compound and/or derivative thereof as described herein are also provided. In some embodiments, the lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing a heterocyclic compound and/or derivative thereof as described herein are also provided. The cream can contain emulsifying agents and/or other stabilizing agents. In some embodiments, the cream is in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some embodiments of a cream formulation, the water-base percentage can be about 60% to about 75% and the oil-base can be about 20% to about 30% of the total, with the other percentages being the emulsifier agent, preservatives and additives for a total of 100%.

Ointments containing a heterocyclic compound and/or derivative thereof as described herein and a suitable ointment base are also provided. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing a heterocyclic compound and/or derivative thereof as described herein, a gelling agent, and a liquid vehicle. Suitable gelling agents include, but are not limited to, modified celluloses, such as hydroxypropyl cellulose and hydroxyethyl cellulose; carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Also described herein are foams that can include a heterocyclic compound and/or derivative thereof as described herein. Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some embodiments, the buffer can be triethanolamine.

Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, the formulations can be provided via continuous delivery of one or more formulations to a patient in need thereof. For topical applications, repeated application can be done or a patch can be used to provide continuous administration of the noscapine analogs over an extended period of time.

Enteral Formulations

The heterocyclic compounds and/or derivatives thereof as described herein can be prepared in enteral formulations, such as for oral administration. The heterocyclic compound and/or derivative thereof as described herein can be according to any of Formulas 1-20 as set forth herein, active derivative thereof, or pharmaceutical salt thereof. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations containing a heterocyclic compound and/or derivative thereof as described herein can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing a heterocyclic compound and/or derivative thereof as described herein can be prepared using one or more pharmaceutically acceptable excipients, including diluents, preservatives, binders, lubricants, disintegrators, swelling agents, fillers, stabilizers, and combinations thereof.

Delayed release dosage formulations containing a heterocyclic compound and/or derivative thereof as described herein can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing a heterocyclic compound and/or derivative thereof as described herein can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Additional Active Agents

In some embodiments, an amount of one or more additional active agents are included in the pharmaceutical formulation containing a heterocyclic compound and/or derivative thereof as described herein, a derivative thereof, or pharmaceutical salt thereof. Suitable additional active agents include, but are not limited to, antipyretics, immunomodulators, analgesics, and anti-infectives. In some embodiments, the additional active agent is a B-lactam antibiotic. Suitable beta-lactam antibiotics are described below.

Suitable antipyretics include, but are not limited to, nonsteroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Suitable anti-infectives include, but are not limited to, amebicides (e.g. nitazoxanide, paromomycin, metronidazole, tnidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpiviirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, beta lactam antibiotics (benzathine penicillin (benzatihine and benzylpenicillin), phenoxymethylpenicillin, cloxacillin, flucoxacillin, methicillin, temocillin, mecillinam, azlocillin, mezlocillin, piperacillin, amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxacillin, dicloxacillin, nafcillin, cefazolin, cephalexin, cephalosporin C, cephalothin, cefaclor, cefamandole, cefuroxime, cefotetan, cefoxitin, cefiximine, cefotaxime, cefpodoxime, ceftazidime, ceftriaxone, cefepime, cefpirome, ceftaroline, biapenem, doripenem, ertapenem, faropenem, imipenem, meropenem, panipenem, razupenem, tebipenem, thienamycin, azrewonam, tigemonam, nocardicin A, taboxinine, and beta-lactam), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Methods of Using the Heterocyclic Compounds and Formulations Thereof

The heterocyclic compounds and formulations thereof described herein can be administered to a subject in need thereof. The subject in need thereof can be infected with or be suspected of being infected with pathogenic bacteria. The subject in need thereof can be symptomatic or asymptomatic.

In embodiments, the amount of the heterocyclic compounds or formulations thereof delivered to the subject in need thereof can be an amount sufficient to inhibit beta lactamase and/or increase the effectiveness of a co-administered beta-lactam antibiotic (i.e. an effective amount). It will be appreciated that co-administered can refer to a beta-lactam antibiotic that is included in the formulation or provided in a dosage form separate from the heterocyclic compound or formulation thereof. The effective amount of the heterocyclic compound or formulation thereof, such as those described herein, can range from about 1 mg/kg to about 500 mg/kg. In some embodiments, the effective amount ranges from about 10 mg/kg to about 100 mg/kg. If further embodiments, the effective amount ranges from about 1 mg to about 1000 mg. In some embodiments, the effective amount can be about 500 mg to about 1000 mg.

Administration of the heterocyclic compounds, derivatives thereof, and/or formulations thereof can be systemic or localized. The compounds and formulations described herein can be administered to the subject in need thereof one or more times per day. In an embodiment, the compound(s) and/or formulation(s) thereof can be administered once daily. In some embodiments, the compound(s) and/or formulation(s) thereof can be administered given once daily. In another embodiment, the compound(s) and/or formulation(s) thereof can be administered is administered twice daily. In some embodiments, when administered, an effective amount of the compounds and/or formulations are administered to the subject in need thereof. The compound(s) and/or formulation(s) thereof can be administered one or more times per week. In some embodiments the compound(s) and/or formulation(s) thereof can be administered 1 day per week. In other embodiments, the compound(s) and/or formulation(s) thereof can be administered 2 to 7 days per week.

In some embodiments, the compound(s) and/or formulation(s) thereof, can be administered in a dosage form. The amount or effective amount of the compound(s) and/or formulation(s) thereof can be divided into multiple dosage forms. For example, the effective amount can be split into two dosage forms and the one dosage forms can be administered, for example, in the morning, and the second dosage form can be administered in the evening. Although the effective amount is given over two doses, in one day, the subject receives the effective amount. In some embodiments the effective amount is about 1 to about 1000 mg per day. The effective amount in a dosage form can range from about 1 mg/kg to about 1000 mg/kg. The dosage form can be formulated for oral, vaginal, intravenous, transdermal, subcutaneous, intraperitoneal, or intramuscular administration. Preparation of dosage forms for various administration routes are described elsewhere herein.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Expression and Purification of Beta-Lactamases.

For his tag KPC-2 beta-lactamase, bacteria were grown overnight at 30 C with shaking in 50 mL LB broth supplemented with 50 μg/mL kanamycin. Two liters of LB broth supplemented with 50 μg/mL kanamycin, 200 mM sorbitol, and 5 mM betaine were each inoculated with 10 mL of overnight bacterial culture. Cultures were then grown at 37 C until an optical density at 600 nm ($OD_{600}$) of 0.6-0.7. Protein expression was then initiated by the addition of IPTG (final concentration 0.5 mM), followed by growth for 16 hr at 20 C. Cells were pelleted by centrifugation and stored at −80 C until further use. The his tag KPC-2 beta-lactamase was purified by nickel affinity chromatography and gel filtration. Briefly, the cell pellets were thawed and re-suspended in 40 mL of buffer A (20 mM Tris-HCl pH 8.0, 300 mM NaCl, 20 mM imidazole) with one complete protease inhibitor cocktail tablet (Roche) and disrupted by sonication, followed by ultracentrifugation to clarify the lysate. After ultracentrifugation, the supernatant was passed through a 0.22 μm filter before loading onto a 5 mL HisTrap HP affinity column (GE Healthcare Life Sciences, USA) pre-equilibrated with buffer A. His tag KPC-2 was eluted by a linear imidazole gradient (20 mM to 500 mM). Fractions were analyzed by SDS-PAGE. Fractions containing his tag KPC-2 were concentrated using a 10 k NMWL Amicon Ultra-15 Centrifugal Filter Unit. Concentrated his tag KPC-2 was then loaded onto a superdex 75 gel filtration column (GE Healthcare Life Sciences) pre-equilibrated with 20 mM Tris-HCl pH 8.0, 300 mM NaCl. Protein concentration was determined by absorbance at 280 using an extinction coefficient of 39,545. SDS-PAGE analysis indicated that the eluted protein was more than 95% pure.

For sumo tag NDM-1 metallo-beta-lactamase, bacteria were grown overnight at 30 C with shaking in 50 mL LB broth supplemented with 100 μg/mL ampicillin. Two liters of LB broth supplemented with 100 μg/mL ampicillin were each inoculated with 10 mL of overnight bacterial culture. Cultures were then grown at 37 C until an optical density at 600 nm ($OD_{600}$) of 0.6-0.7. Protein expression was then initiated by the addition of IPTG (final concentration 0.5 mM), followed by growth for 16 hr at 20 C. Cells were pelleted by centrifugation and stored at −80 C until further use. The sumo tag NDM-1 beta-lactamase was purified by nickel affinity chromatography and gel filtration. Briefly, the cell pellets were thawed and re-suspended in 40 mL of buffer A (20 mM HEPES pH 7.4, 0.5 M NaCl, 20 mM imidazole) with one complete protease inhibitor cocktail tablet (Roche) and disrupted by sonication, followed by ultracentrifugation to clarify the lysate. After ultracentrifugation, the supernatant was passed through a 0.22 μm filter before loading onto a 5 mL HisTrap HP affinity column (GE Healthcare Life Sciences, USA) pre-equilibrated with buffer A. Sumo tag NDM-1 was eluted by a linear imidazole gradient (20 mM to 500 mM). Fractions were analyzed by SDS-PAGE. Fractions containing sumo tag NDM-1 were buffer exchanged into 20 mM HEPES pH 7.0, 100 mM NaCl. Cleavage of the sumo tag was then carried out with ULP1 protease overnight at room temperature and then concentrated using a 10 k NMWL Amicon Ultra-15 Centrifugal Filter Unit. The sample was then loaded back onto a nickel affinity column and the flow through was collected, containing the untag NDM-1. NDM-1 was concentrated and loaded onto a gel filtration column (GE Healthcare Life Sciences) pre-equilibrated with 20 mM HEPES pH 7.0, 100 mM NaCl. Protein concentration was determined by absorbance at 280 using an extinction coefficient of 27,960. SDS-PAGE analysis indicated that the eluted protein was more than 95% pure.

Steady-state kinetic analysis. Steady-state kinetic parameters were determined by using a Biotek Cytation Multi-Mode Reader. For KPC-2, each assay was performed in 100 mM Tris-HCl pH 7.0, 0.01% Triton X-100 at 37 C. $V_{max}$ and $K_m$ were determined from initial steady-state velocities from nitrocefin read at a wavelength of 486 nm. The kinetic parameters were obtained using the non-linear portion of the data to the Henri-Michaelis (equation 1) using SigmaPlot 12.5.

$$V = V\max[S]/(K_m + [S]) \quad \text{Equation (1)}$$

$IC_{50}$, defined as the inhibitor concentration that results in a 50% reduction of nitrocefin (20 μm) hydrolysis was determined by measurements of initial velocities after mixing 1 nM of KPC-2 with increasing concentrations of inhibitors. The inhibition constant ($K_i$) was calculated according to equation 2:

$$K_i = IC_{50}/([S]/K_m + 1) \quad \text{Equation (2)}$$

For NDM-1, the procedures were the same as above except the assay was performed in 100 mM Tris-HCl pH 7.0, 1 μM $ZnSO_4$, 0.01% Triton X-100. Steady-state kinetic parameters are shown in Table 1. Table 1 demonstrates inhibition of KPC-2 and NDM-1 by compounds of the disclosed herein. Compounds according to Formulas 5-10 were purchased from commercial sources. The last compound was de novo synthesized.

TABLE 1

| Compound Number | Structure | $K_i$ (KPC-2) (μM) | $K_i$ (NDM-1) (μM) | His-Tag KPC-2 Ki (μM) | NDM-1 Ki (μM) | VIM-2 Ki (μM) | His-tag SHV-2 Ki (μM) |
|---|---|---|---|---|---|---|---|
| 72875 | Formula 5 | 13.4 | | | | | |
| 72588 | Formula 6 | 1.5 | ~100 | | | | |
| 73043 | Formula 7 | 26.6 | | | | | |
| 73475 | Formula 8 | 13.5 | | | | | |
| 72674 | Formula 9 | 154.4 | | | | | |

TABLE 1-continued

| Compound Number | Structure | $K_i$ (KPC-2) (μM) | $K_i$ (NDM-1) (μM) | His-Tag KPC-2 Ki (μM) | NDM-1 Ki (μM) | VIM-2 Ki (μM) | His-tag SHV-2 Ki (μM) |
|---|---|---|---|---|---|---|---|
| 73152 | Formula 10 | 39.5 | | | | | |
| 994284 | Formula 11 | 5.7 | | | | | |
| 994942 | Formula 13 | | | 0.4881 | 54.97 | 1.8 | No inhibition |
| 994943 | Formula 14 | | | 122 | | 9.12 | |
| 995015 | Formula 15 | | | 8.9 | | 4.7 | |
| 995016 | Formula 18 | | | 447.1 | | 24.33 | |
| 995018 | Formula 16 | | | 79.2 | | 15.57 | |
| 995019 | Formula 19 | | | precipitation | precipitation | precipitation | precipitation |
| 1014507 | Formula 17 | | | 4.22 | | | |

Mic Studies.

Compounds were tested for synergy with the carbapenem antibiotic, imipenem, against BL21(DE3) *E. coli* expressing KPC-2. MIC values were determined with the Mueller-Hinton broth microdilution method. To test for inhibitory activity, compounds were dissolved in DMSO and dilutions were carried out using LB broth. Compounds were test at 100 μM with increasing concentrations of imipenem. A control was performed with DMSO to demonstrate that DMSO did not have an effect on bacteria growth. After inoculation, the plates are incubated at 37 C for 24 hours. The MIC of the compounds were then determined visually. MIC data are shown in Tables 2 and 3. Tables 2 and 3 demonstrate MICs of imipenem when combined with select coumarin phosphonate derivatives. For Table 3, 16 μg/mL of compounds were tested for synergy with the carbapenem antibiotic, imipenem, against a *K. pneumoniae* strain expressing KPC-2.

TABLE 2

| | MIC (μg/mL) | | | | |
|---|---|---|---|---|---|
| Strain | Imipenem | Imipenem + 72588 | Imipenem + 72875 | Imipenem + 73043 | Imipenem + 73475 |
| *E. coli* BL21(DE3) pET-GST-bla$_{KPC-2}$ | 4 | 0.5 | 1 | 1 | 1 |

TABLE 3

| | | | MIC (μg/mL) | | | | |
|---|---|---|---|---|---|---|---|
| Organism | ATCC | Phenotype | 73043 (Formula 7) | 72588 (Formula 6) | IMP | IMP/ Formula 7 | IMP/ Formula 6 |
| *K. pneumoniae* | 4683 | KPC-2 | >32 | >32 | 8 | 8 | 4 |

Crystallization and Soaking Experiments.

Crystallization trials were carried out by using Qiagen crystallization kits. An initial condition was found in the Classics suite A4 containing 2 M Ammonium sulfate and 5% (v/v) isopropanol. Crystals of his tag KPC-2 were grown at 20 C using the hanging-drop vapor diffusion in EasyXtal 15-Well tools (Qiagen). Protein solutions (10-20 mg/ml) in 20 mM Tris-HCl pH 8.0, 300 mM NaCl were mixed 1:2 (v/v) with a reservoir solution containing 2 M ammonium sulfate and either 5% (v/v) isopropanol or 5% (v/v) ethanol. Droplets (1.5 μL) were microseeded with 0.5 μL of diluted seed stock. Crystals typically began to form within two weeks. To obtain the inhibitor bound structures, KPC-2 crystals were soaked in a solution containing 1.44 M sodium citrate and 10 mM of coumarin phosphonate derivative for 1 hour. The soaked crystals were cryo-protected in a solution containing 1.15 M sodium citrate, 20% (v/v) glycerol, and 0.5 mM coumarin phosphonate derivative and flash-frozen in liquid nitrogen.

Data Collection and Structure Determinations.

Figure 1B:
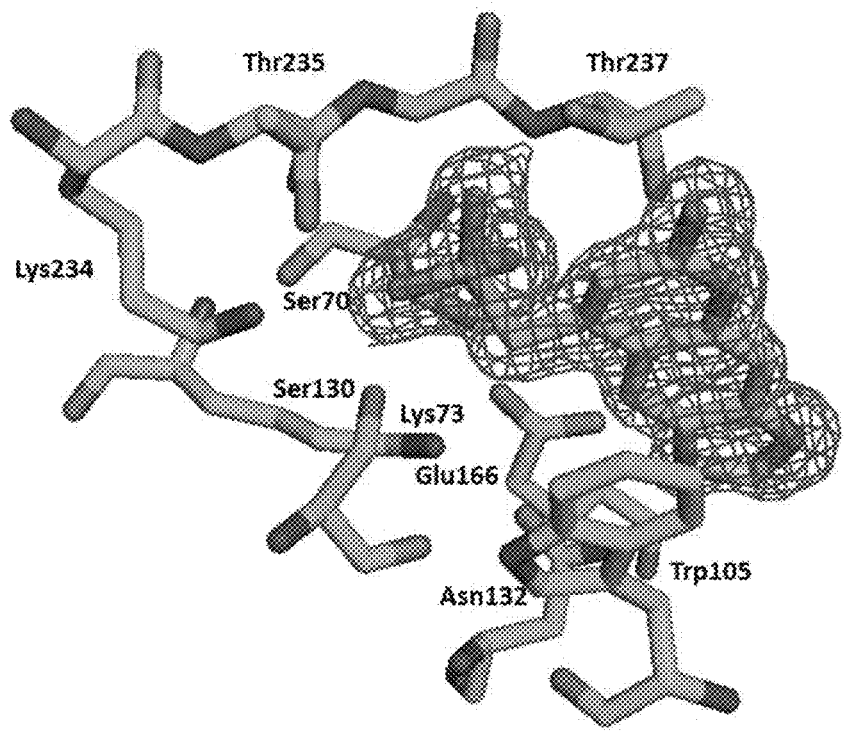
Figure 1C:
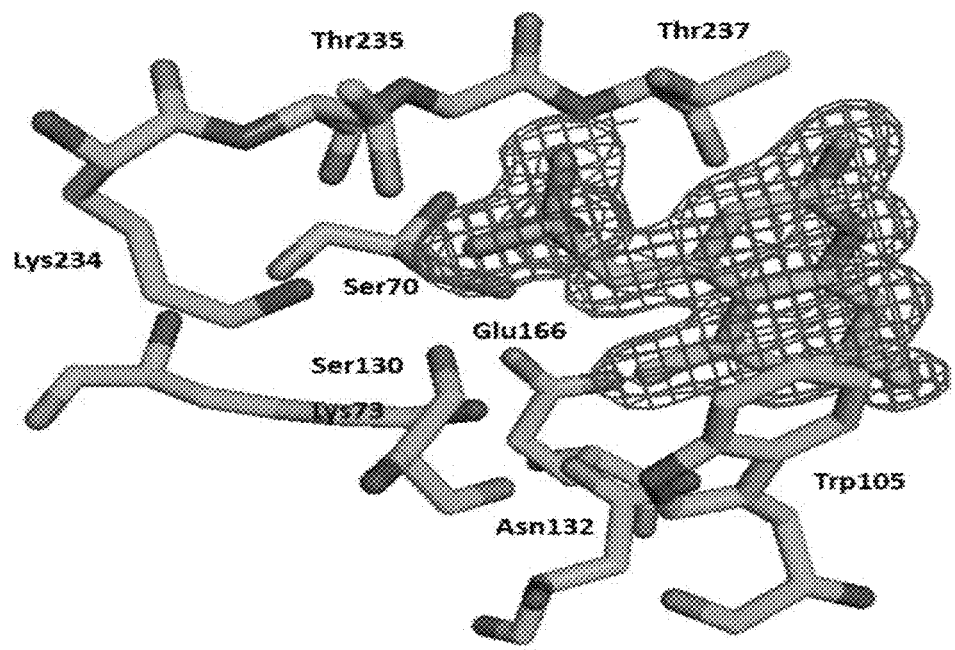
Figure 1D:
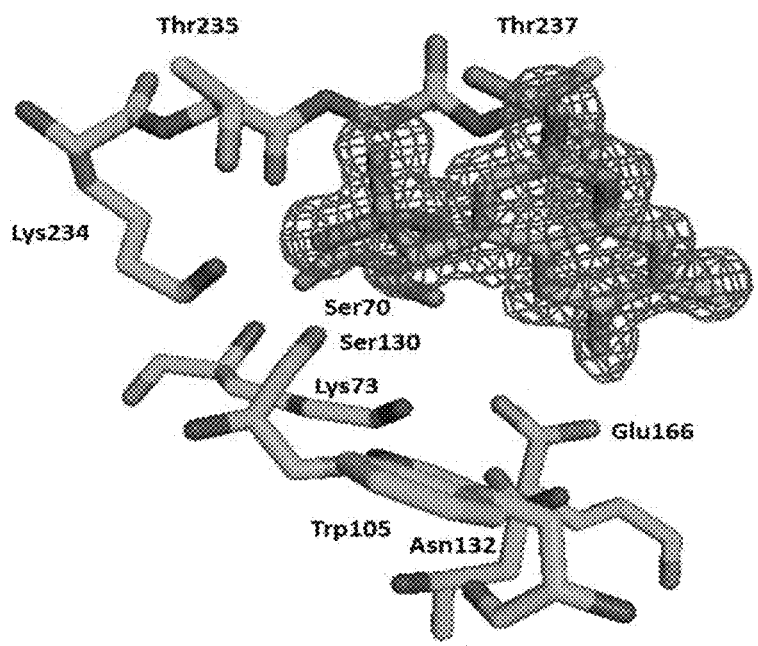
Figure 1E:
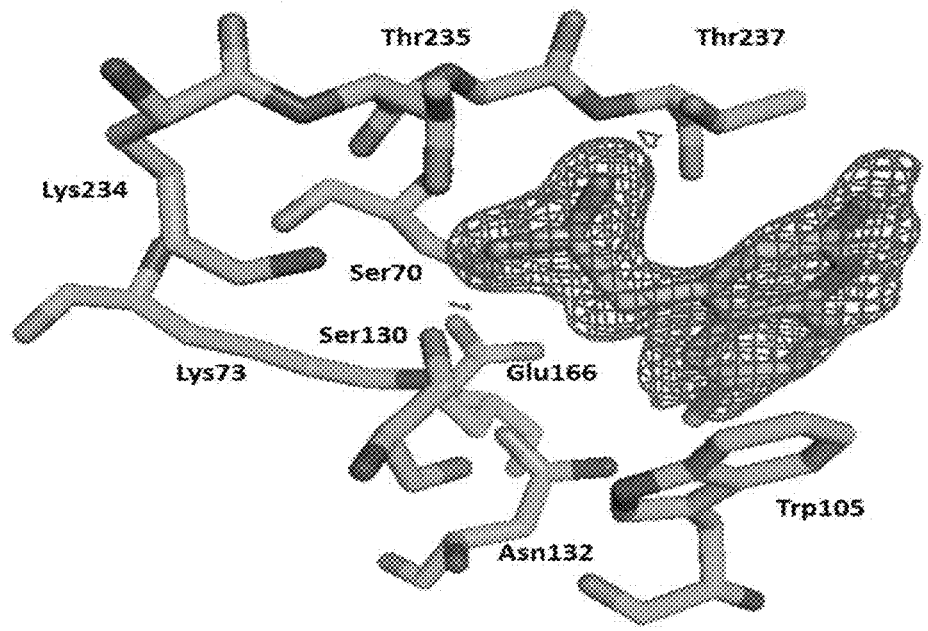
Figure 1F:
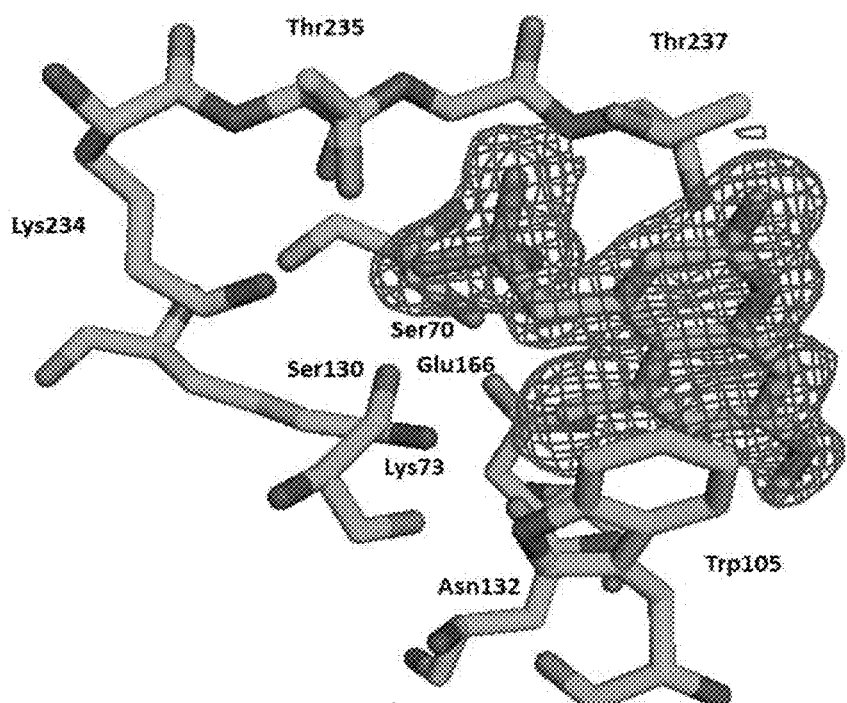
Figure 1G:
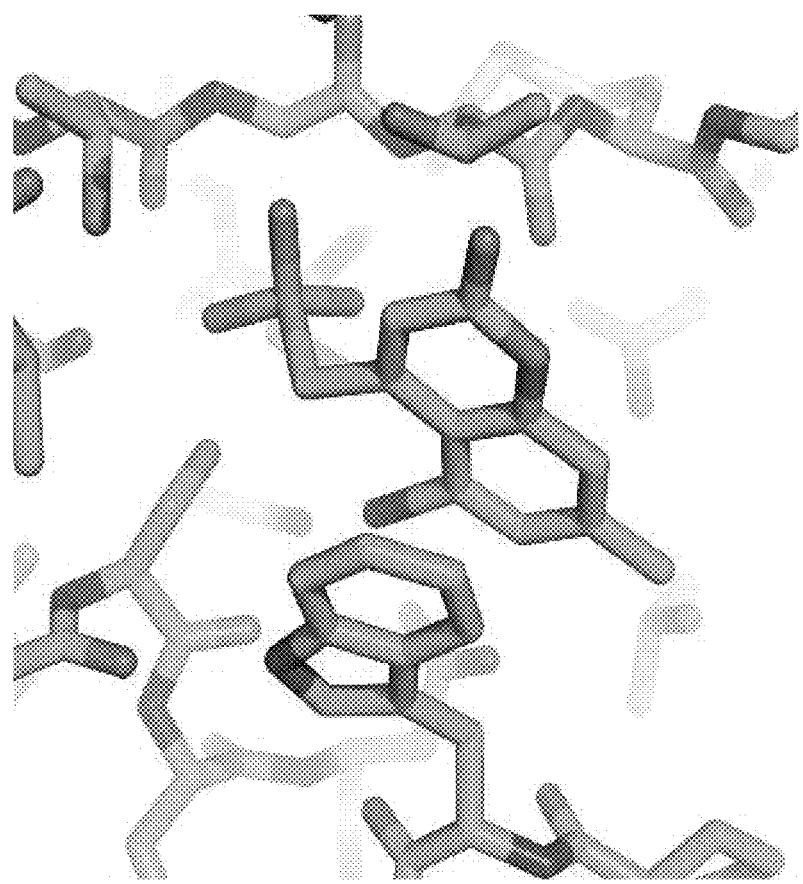
Figure 2A:
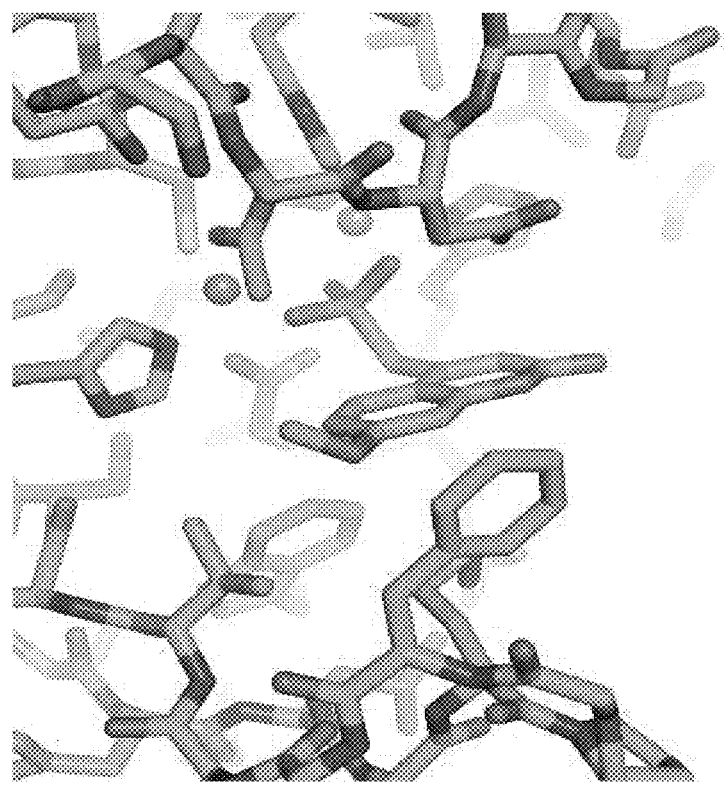
FIGS. 2A-2H show crystal structures of NDM-1 bound with (FIG. 2A) 72875 (Formula 5), (FIG. 2B) 73043 (Formula 7), (FIG. 2C) 994284 (Formula 11), (FIG. 2D) 994942 (Formula 13), (FIG. 2E) 994943 (Formula 14), (FIG. 2F) 995016 (Formula 18), (FIG. 2G) 995018 (Formula 16), and (FIG. 2H) 1014507 (Formula 17).
Figure 2B:
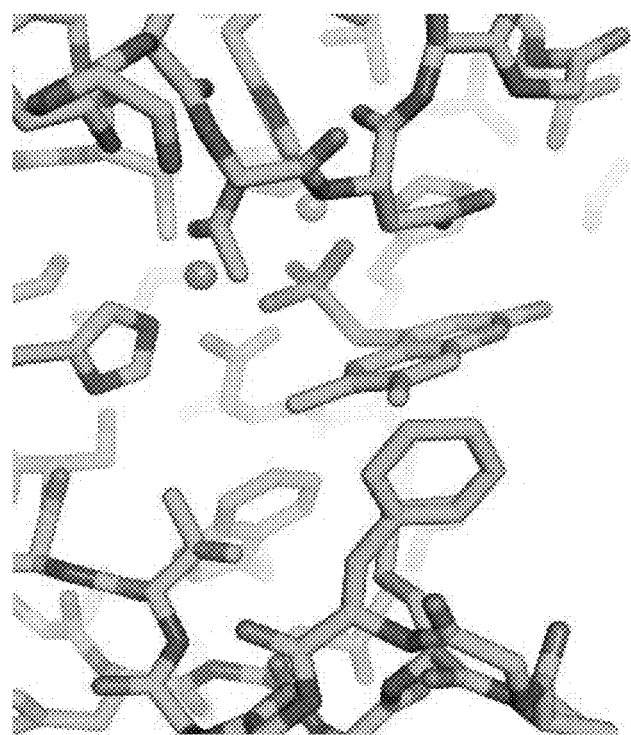
Figures 2C, 2D:
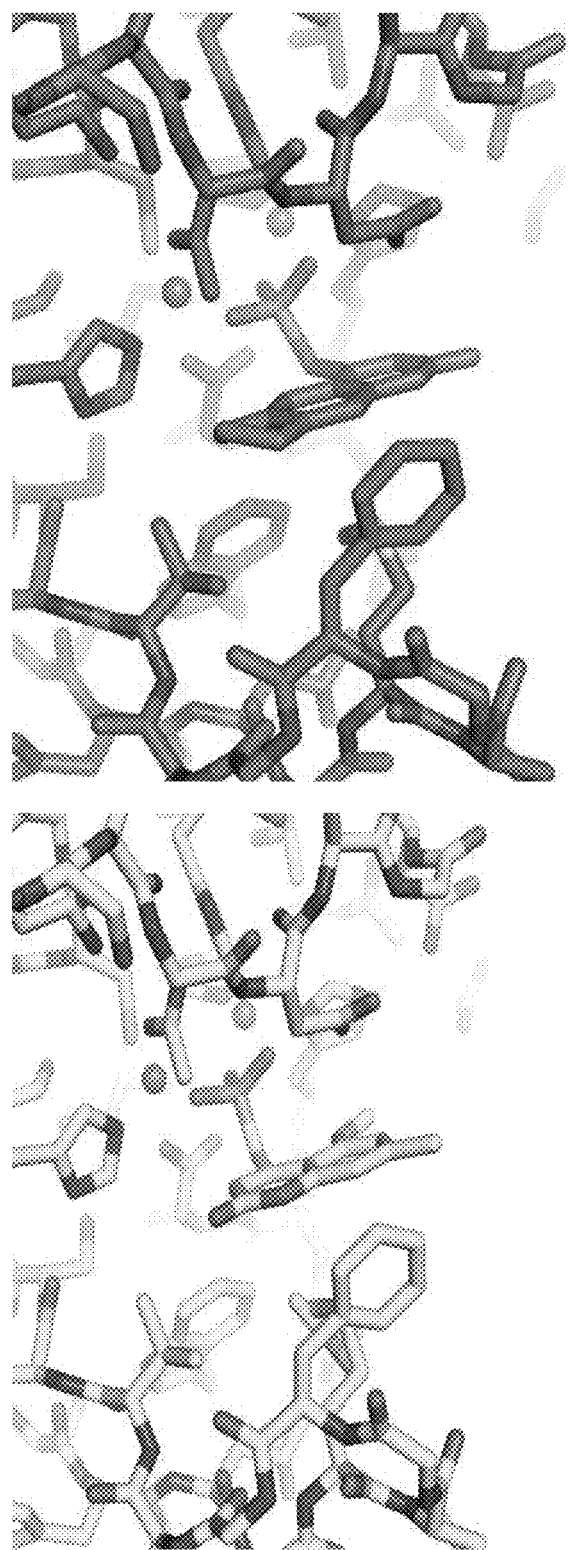
Figure 2E:
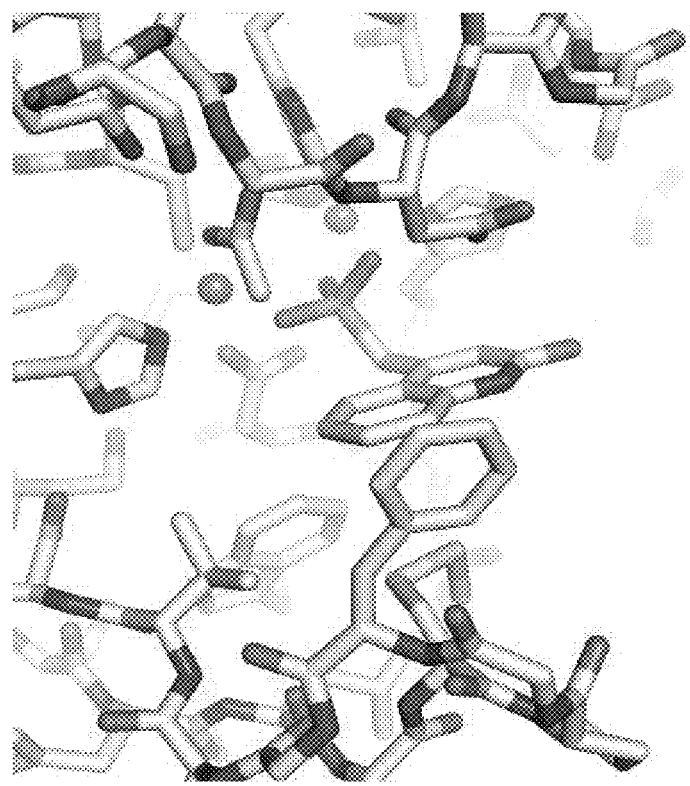
Figure 2F:
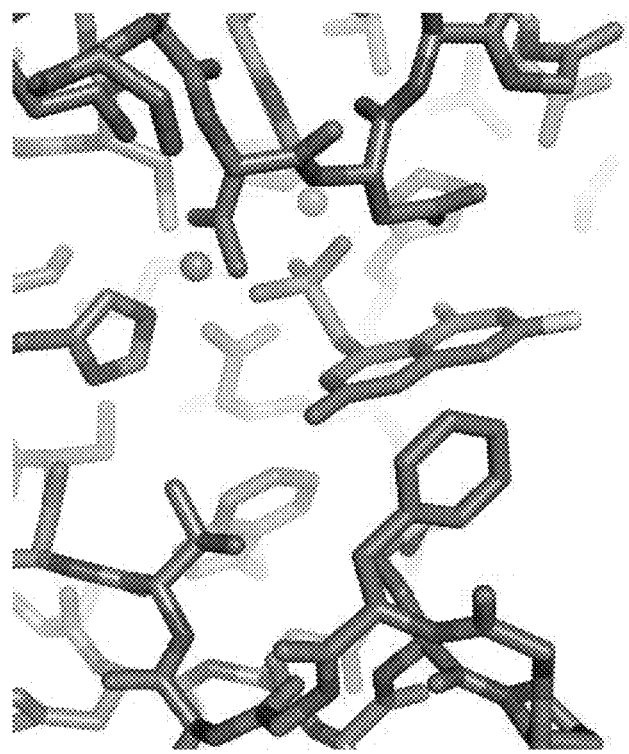
Figures 2G, 2H:
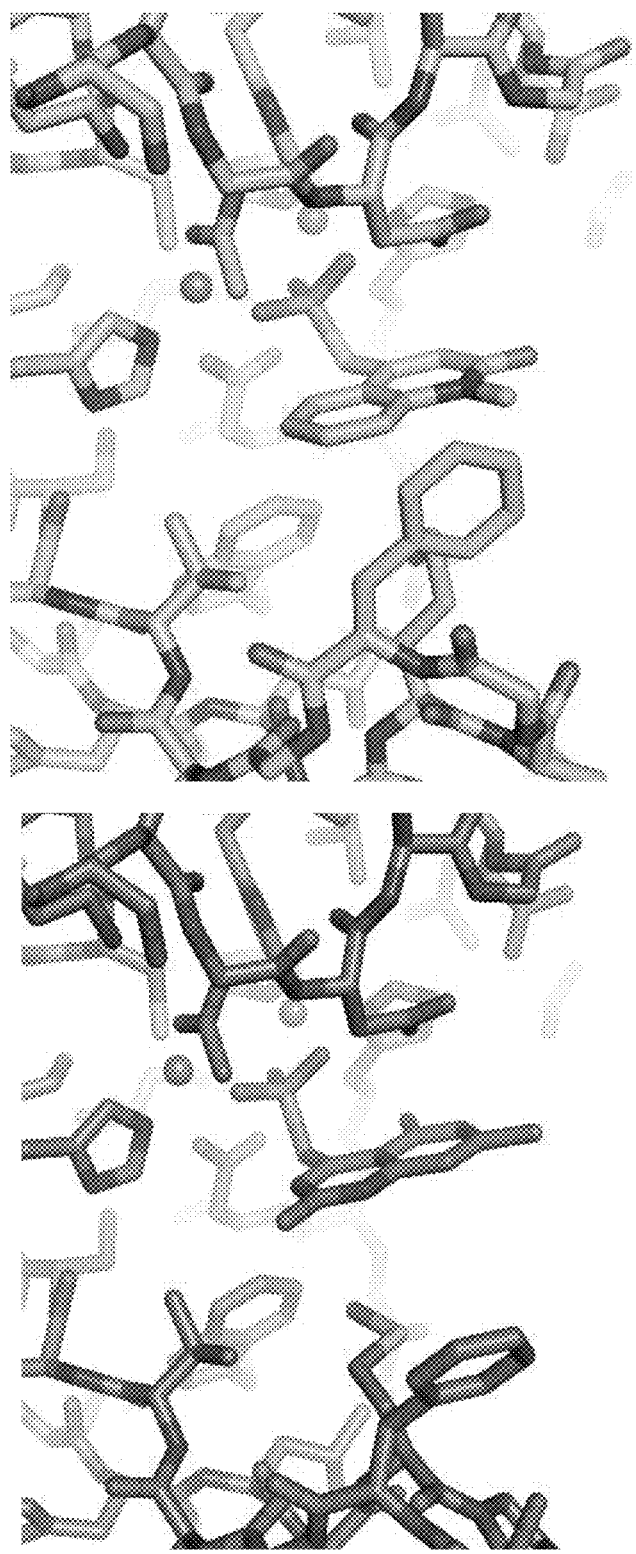
Figure 3A:
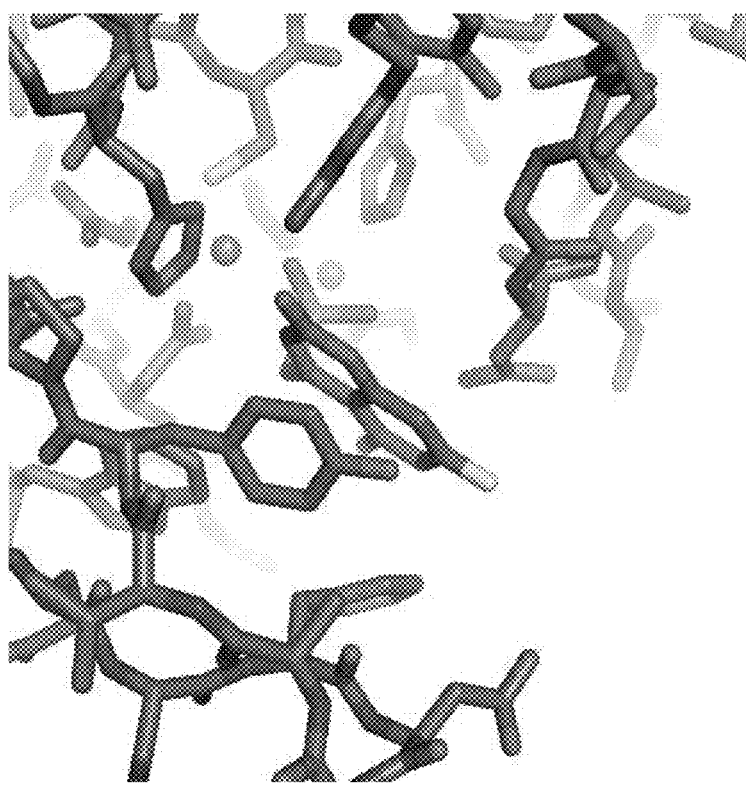
FIGS. 3A-3B show crystal structures of VIM-2 bound with (FIG. 3A) 995015 (Formula 15) and (FIG. 3B) 995016 (Formula 18).
Figure 3B:
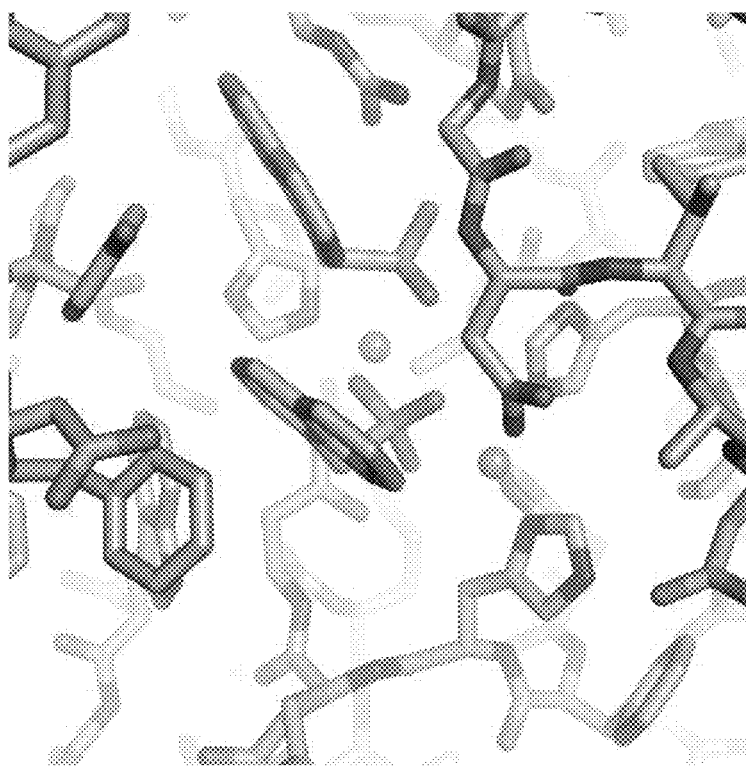

Data for the KPC-2 complex structures were collected at the Advanced Photon Source (APS) beamline 22-ID-D and at the Advanced Light Source (ALS) beamline 8.3.1. Diffraction data were indexed and integrated with iMosflm and scaled with SCALA from the CCP4 suite. Phasing was performed using molecular replacement with the program Phaser with the truncated KPC-2 structure (PDB 3C5A). Structure refinement was performed using phenix.refine and model building in WinCoot. The program eLBOW in Phenix was used to obtain geometry restraint information for the coumarin phosphonate derivatives. The final model qualities were assessed using MolProbity. The structures of select compounds are shown in FIGS. 1A-3B.

We claim:
1. A compound according to Formula 1,

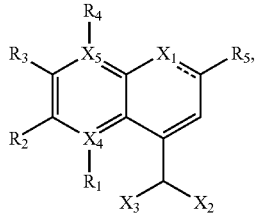

Formula 1 wherein $X_1$ is O, CH, or N—$R_8$, wherein $R_8$ is $CH_3$ or H;
wherein $X_2$ is $PO(OH)_2$;
wherein $X_3$ is H;
wherein $X_4$ is C or $N^+$;
wherein $X_5$ is C;
wherein $R_1$ is $CH_3$, Br, F, $O^-$, or $OCH_3$;
wherein $R_2$ is H;
wherein $R_3$ is H, $CH_3$, F, or $OCH_3$;
wherein $R_4$ is H;
wherein $R_5$ is H or =O; and
wherein $R_1$ and $R_3$ are not both $CH_3$ if $X_1$ is O, and wherein $R_3$ is not $OCH_3$ if $X_1$ is O and $R_1$ is $CH_3$.

2. The compound of claim 1, wherein the compound is a compound according to any one of Formulas 12-13, 15, 17 and 19:

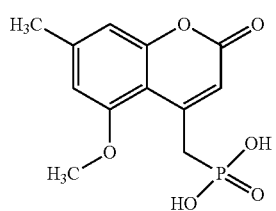

Formula 12

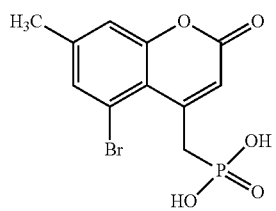

Formula 13

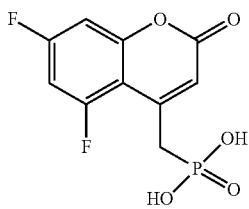

Formula 15

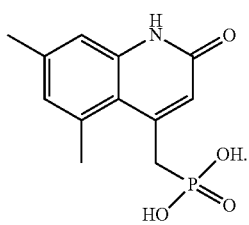

Formula 17

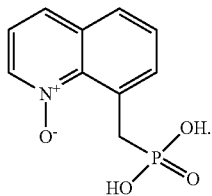

Formula 19

3. The compound of claim 1, wherein the compound is a compound according to Formula 2

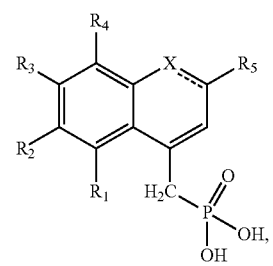

Formula 2 wherein X is O or N—$R_9$, wherein $R_9$ is H or $CH_3$;
wherein $R_1$ is $CH_3$, Br, F, or $OCH_3$;
wherein $R_2$ is H;
wherein $R_3$ is H, $CH_3$, F, or $OCH_3$;
wherein $R_4$ is H;
wherein $R_5$ is H or =O; and
wherein $R_1$ and $R_3$ are not both $CH_3$ if X is O, and wherein $R_3$ is not $OCH_3$ if $X_1$ is O and $R_1$ is $CH_3$.

4. The compound of claim 3, wherein the compound is a compound according to any one of Formulas 12-13, 15, and 17:

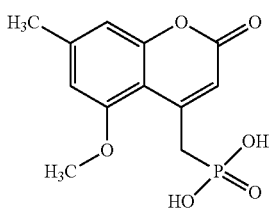

Formula 12

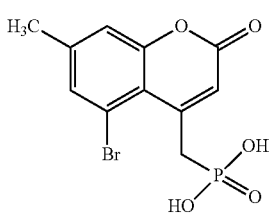

Formula 13

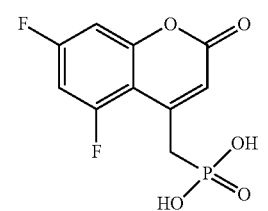

Formula 15

-continued

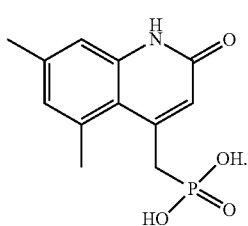

Formula 17

5. A pharmaceutical formulation comprising:
an amount of a compound according to Formula 1

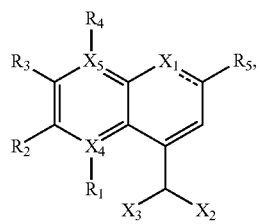

Formula 1 wherein $X_1$ is O, CH, or N—$R_8$, wherein $R_8$ is $CH_3$ or H;
wherein $X_2$ is $PO(OH)_2$;
wherein $X_3$ is H;
wherein $X_4$ is C or $N^+$;
wherein $X_5$ is C;
wherein $R_1$ is $CH_3$, Br, F, $O^-$, or $OCH_3$;
wherein $R_2$ is H;
wherein $R_3$ is H, $CH_3$, F, or $OCH_3$;
wherein $R_4$ is H;
wherein $R_5$ is H or =O; and
wherein $R_1$ and $R_3$ are not both $CH_3$ if $X_1$ is O, and wherein $R_3$ is not $OCH_3$ if $X_1$ is O and $R_1$ is $CH_3$.

6. The pharmaceutical formulation of claim 5, further comprising a pharmaceutically acceptable carrier.

7. The pharmaceutical formulation of claim 5, further comprising a beta lactam antibiotic.

8. The pharmaceutical formulation of claim 5, wherein the compound according to Formula 1 is present in the formulation at an amount effective to increase the efficacy of a beta lactam antibiotic or reduce the amount of or the activity of a beta lactamase.

9. The pharmaceutical formulation of claim 5, wherein the compound is a compound according to any one of Formulas 12-13, 15, 17 and 19:

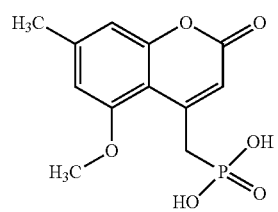

Formula 12

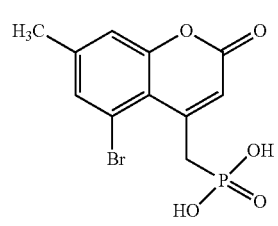

Formula 13

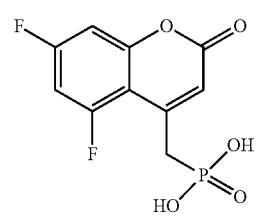

Formula 15

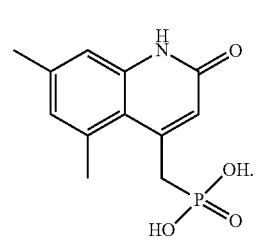

Formula 17

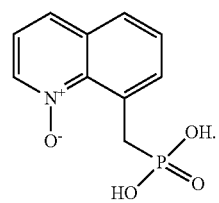

Formula 19

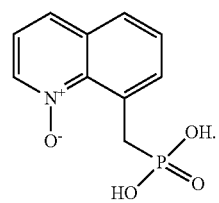

10. The pharmaceutical formulation of claim 5, wherein the compound is a compound according to Formula 2

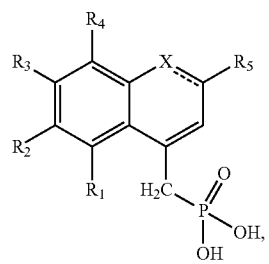

Formula 2 wherein X is O or N—$R_9$, wherein $R_9$ is H or $CH_3$;
wherein $R_1$ is $CH_3$, Br, F, or $OCH_3$;
wherein $R_2$ is H;
wherein $R_3$ is H, $CH_3$, F, or $OCH_3$;
wherein $R_4$ is H;
wherein $R_5$ is H or =O; and
wherein $R_1$ and $R_3$ are not both $CH_3$ if X is O, and wherein $R_3$ is not $OCH_3$ if $X_1$ is O and $R_1$ is $CH_3$.

11. The pharmaceutical formulation of claim 10, wherein the compound is a compound according to any one of Formulas 12-13, 15, and 17

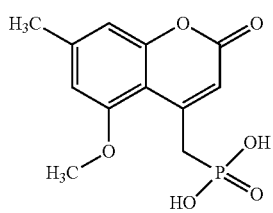

Formula 12

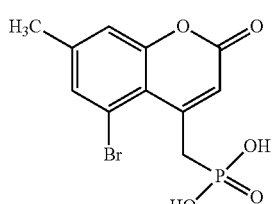

Formula 13

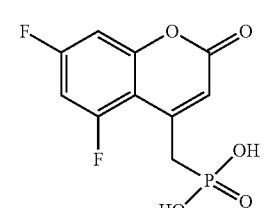

Formula 15

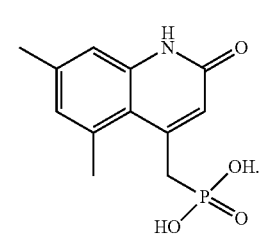

Formula 17

12. A method of treating a pathogenic bacterial infection in a subject in need thereof, the method comprising:
administering, to the subject in need thereof having a pathogenic bacterial infection, an amount of a compound according to Formula 1

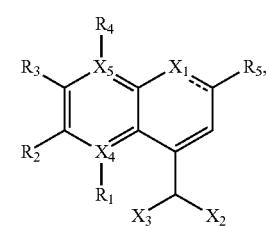

Formula 1 wherein $X_1$ is O, CH, or N—$R_8$, wherein $R_8$ is $CH_3$ or H;
wherein $X_2$ is $PO(OH)_2$;
wherein $X_3$ is H;
wherein $X_4$ is C or $N^+$;
wherein $X_5$ is C;
wherein $R_1$ is $CH_3$, Br, F, $O^-$, or $OCH_3$;
wherein $R_2$ is H;
wherein $R_3$ is H, $CH_3$, F, or $OCH_3$;
wherein $R_4$ is H;
wherein $R_5$ is H or =O; and
wherein both $R_1$ and $R_3$ are not both $CH_3$ if $X_1$ is O, and
wherein $R_3$ is not $OCH_3$ if $X_1$ is O and $R_1$ is $CH_3$.

13. The method of claim 12, wherein the pathogenic bacterial infection is caused by a pathogenic bacteria is resistant to at least one beta-lactam antibiotic.

14. The method of claim 12, further comprising administering a beta lactam antibiotic to the subject in need thereof.

15. The method of claim 12, wherein the compound according to Formula 1 is present in the formulation at an amount effective to increase the efficacy of a beta lactam antibiotic or reduce the amount of or the activity of a beta lactamase.

16. The method of claim 12, wherein the compound is a compound according to any one of Formulas 12-13, 15, 17, and 19:

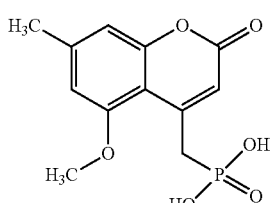

Formula 12

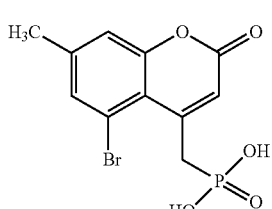

Formula 13

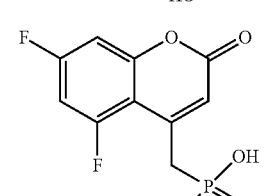

Formula 15

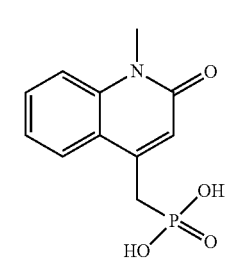

Formula 16

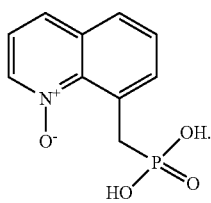

Formula 19

17. The method of claim 12, wherein the compound is a compound according to Formula 2

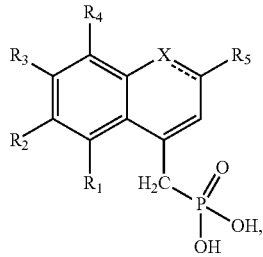

Formula 2 wherein X is O or N—$R_9$, wherein $R_9$ is H or $CH_3$;
wherein $R_1$ is $CH_3$, Br, F, or $OCH_3$;
wherein $R_2$ is H;
wherein $R_3$ is H, $CH_3$, F, or $OCH_3$;
wherein $R_4$ is H;
wherein $R_5$ is H or =O; and
wherein $R_1$ and $R_3$ are not both $CH_3$ if X is O, and wherein $R_3$ is not $OCH_3$ if $X_1$ is O and $R_1$ is $CH_3$.

18. The method of claim 17, wherein the compound is a compound according to any one of Formulas 12-13, 15, and 17

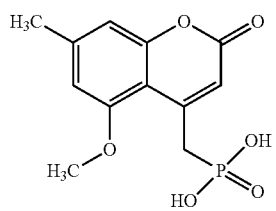

Formula 12

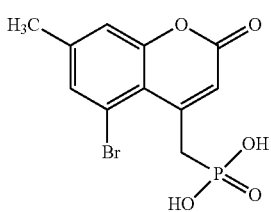

Formula 13

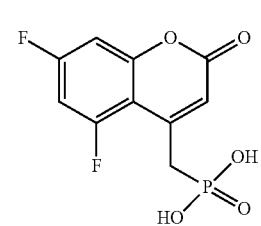

Formula 15

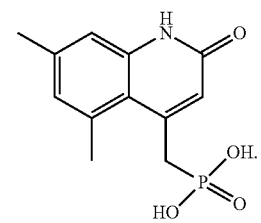

Formula 17

* * * * *